US006255341B1

(12) United States Patent
DeMichele et al.

(10) Patent No.: US 6,255,341 B1
(45) Date of Patent: *Jul. 3, 2001

(54) PRODUCT AND METHOD REDUCE STRESS INDUCED IMMUNE SUPPRESSION

(75) Inventors: Stephen J. DeMichele, Dublin; John W. McEwen, Gahanna; Steven M. Wood, Pickerington, all of OH (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/267,557

(22) Filed: Mar. 12, 1999

Related U.S. Application Data

(63) Continuation-in-part of application No. 09/028,987, filed on Feb. 25, 1998, now Pat. No. 6,130,244.

(51) Int. Cl.[7] .............................. A23L 1/30; A23L 1/302; A23L 1/304; A23L 1/305; A61K 31/375

(52) U.S. Cl. .................. 514/474; 424/195.1; 424/600; 424/630; 424/638; 424/641; 424/643; 424/702; 514/2; 514/7; 514/12; 514/23; 514/52; 514/54; 514/168; 514/249; 514/400; 514/419; 514/423; 514/458; 514/494; 514/499; 514/500; 514/546; 514/547; 514/549; 514/552; 514/556; 514/558; 514/561; 514/562; 514/564; 514/565

(58) Field of Search ........................... 514/904, 905, 514/474, 458, 725, 763, 547, 558, 560, 494, 499, 500, 249, 400, 419, 423, 556, 561, 562, 564, 565, 567, 23, 53, 54, 2, 7, 12, 52, 168, 549, 706, 786; 424/702, 630, 641, 195.1, 600, 638, 643

(56) References Cited

U.S. PATENT DOCUMENTS

| Re. 37,020 | * | 1/2001 | Lin et al. ............................... 514/52 |
| 4,607,052 | | 8/1986 | Mendy et al. ........................ 514/547 |
| 4,871,768 | | 10/1989 | Bistrian et al. ....................... 514/547 |
| 4,981,844 | | 1/1991 | Alexander et al. .................... 514/21 |
| 5,223,285 | | 6/1993 | DeMichele et al. ................... 426/72 |
| 5,360,821 | | 11/1994 | Leung ................................... 514/563 |
| 5,444,054 | | 8/1995 | Garleb et al. .......................... 514/54 |
| 5,556,644 | | 9/1996 | Chandra ............................... 424/630 |

FOREIGN PATENT DOCUMENTS

| 0 721 742 | 7/1996 | (EP) . |
| WO 96/31457 | 10/1996 | (WO) . |
| WO 97 39749 | 10/1997 | (WO) . |

OTHER PUBLICATIONS

Bendich A: "Antioxidant Vitamins and Their Function in Immune Responses" Advances in Experimental Medicine and Biology, No. 262, Jan. 1, 1990, p. 35.

Pederson, B.K., et al., "The Immune System During Exposure to Extreme Physiologic Conditions," *Int. J. Sports Med.*, 15, 1994, pp. S116–S121.

Chandra, R.K., "Effect of Vitamin and Trace–Element Supplementation on Immune Responses and Infection in Elderly Subjects," *The Lancet*, 1992; vol. 340: pp. 1124–1127.

Christou, N.V., et al., "Two Techniques of Measurement of the Delayed Hypersensitivity Skin Test Response for the Assessment of Bacterial Host Resistance,"*World J. Surg.*, 1985, vol. 9, pp. 798–806.

Christou, N.V., et al., "The Delayed Hypersensitivity Response and Host Resistance in Surgical Patients, 20 Years Later," *Annals of Surgery*, 1995, vol. 222, No. 4., pp. 534–548.

Dorian, B. and Garfinkel, P.E., "Stress, Immunity and Illness—A Review," *Physiological Medicine*, 1987, vol. 17, pp. 393–407.

Heath, G.W., et al., "Exercise and Upper Respiratory Tract Infections, Is There a Relationship?," *Sports Medicine*, 1992, vol. 14(6), pp. 353–365.

Grimble, R.F., "Malnutrition and the Immune Response," *Transactions of the Royal Society of Tropical Medicine and Hygiene*, 1994, vol. 88, pp. 615–619.

Keusch, G. T., "Antioxidants in Infection," *J. Nutr. Sci, Vitaminol.*, 1993, pp. S23–S33.

Aruoma, O.I., "Free Radicals and Antioxidant Strategies in Sports," *J. Nutr. Biochem.*, 1994, vol. 5, 1994.

Clarkson, P.M., "Antioxidants and Physical Performance," *Critical Reviews in Food Science and Nutrition*, 1995, vol. 35 (1 & 2), pp. 131–141.

Bernton, E., et al., "Adaptation to Chronic Stress in Military Trainees," *Annals of New York Academy of Sciences*, 1995, vol. 774, pp. 217–231.

Boyum, A., et al., "The Effect of Strenuous Exercise, Calorie Deficiency and Sleep Deprivation on White Blood Cells, Plasma Immunoglobulins and Cytokines," *Scand. J. Immunol.*, 1996, vol. 43, pp. 228–235.

Nieman, D.C., et al., "Role of Endurance Exercise in Immune Senescence," Medicine and Science in Sports and Exercise, 1994, pp. 172–181.

Fitzgerald, L., "Overtraining Increases the Susceptibility to Infection," *International Journal of Sports Medicine*, 1991, vol. 12, pp. S5–S8.

Nieman, D.C., "Exercise, Upper Respiratory Tract Infection, and the Immune System," *Medicine and Science in Sports and Exercise*, 1994, pp. 128–139.

Singh, V.N., "A Current Perspective on Nutrition and Exercise," *American Institute of Nutrition*, 1992, pp. 760–765.

* cited by examiner

*Primary Examiner*—John Pak
(74) *Attorney, Agent, or Firm*—J. Michael Dixon

(57) ABSTRACT

In its broadest aspect, the present invention is directed to the discovery of immunonutritional products that are useful in reducing the immunological system suppression that results from stress. The stress may be in the form of physical exertion, mental exhaustion, disease states and the like. In one embodiment, the invention relates to a nutritional composition comprising a structured glyceride component and an antioxidant system. This nutritional composition has been shown to be highly effective in reducing immune system down regulation or dysregulation as a result of stress.

26 Claims, 7 Drawing Sheets

PRODUCT AND METHOD REDUCE STRESS INDUCED IMMUNE SUPPRESSION

RELATED APPLICATIONS

This application is a continuation-in-part of U.S. patent application Ser. No. 09/028,987, filed Feb. 25, 1998, Now U.S. Pat. No. 6,130,244 the contents of which are hereby incorporated by reference.

TECHNICAL FIELD

This invention relates to a method to reduce stress induced suppression of the immune system of an animal. The method comprises administering to an animal, prior to, during and/or subsequent to the stress event, a nutritional product comprising a structured glyceride component and an antioxidant system. The invention also relates to a nutritional product that comprises an antioxidant system and a structured glyceride component.

BACKGROUND

Stress is a physical, chemical or emotional factor that causes bodily or mental tension and may be a factor in disease causation. The notion that excessive stress can alter host defenses and increase susceptibility to illness is not new. A publication by Pedersen, et al., provides a review of work conducted in the area of stress and disease. See Pedersen, et al., "The immune system during exposure to extreme physiological conditions", Inter J. Sports Med. 1994 15:5116–5121.

In recent years, rapid advances in the field of immunology have generated intense interest in the interaction between stress induced by psychosocial, nutritional and physical factors and the immune system. A major premise of this work is that stress may enhance vulnerability to disease by exerting an immunosuppressive effect. This may especially be true of diseases intimately connected with immunologic mechanisms such as infection, malignancy and autoimmune disease.

Studies demonstrating immune alterations in human stress encompass a number of models wherein most types of experimental and naturally occurring stresses have been associated with alteration of the components of the immune system. Some of the earliest work was done by the United States National Aeronautic Space Administration (NASA). The NASA studies showed that white blood cells and T-lymphocytes were elevated during the splash-down phase of space flight. However, there was impairment in the lymphoproliferative response to mitogenic stimulation during the first three (3) days after return to earth. A slight decrease in the stimulation response of lymphocytes was also observed prior to launch, possibly due to anticipation. A good overview of stress and immune function can be found in "Stress, Immunity and Illness—A Review", authored by Dorian and Garfinkel, *Psychological Medicine*, 17:393–407 (1987).

Physical activity and exercise are also known to produce a variety of alterations to the immune system. The effects of vigorous exercise appear to depress immune function and may compromise host defenses against upper respiratory tract infections. Epidemiological studies have generally shown a greater risk of upper respiratory tract infections with vigorous levels of exercise. See Heath, et al., "Exercise and Upper Respiratory Tract Infections", *Sports Medicine*, 14(6) 353–365 (1992).

As humans age, they experience a decline in most cell mediated and humoral immune responses. The elderly are often stressed from various infections, bereavement, cancer and nutritional deficiencies. The elderly are also often stressed from environmental factors such as inadequate housing and mental deficiencies. Supplementation with modest physiological amounts of micronutrients has been shown to decrease nutritional deficiencies and improve various measures of immunity and decrease the frequency of infection-related illnesses in ninety six (96) elderly subjects (mean age 75). See Chandra R. K., "Effect of Nutrients and Trace Element Supplementation on Immune Responses and Infection in Elderly Subjects;" Lancet 1992, Vol. 340, pp. 1124–1127. The factors of age, exercise, malnutrition and stress have also been investigated by Hoffman-Goetz, L., et al., "Exercise and Immune Function", CRC Press, Boca Raton (1996).

Infection is characterized by a loss of tissue lipid, protein and micronutrients. This is partially the result of the cytokine mediated response designed to support the activities of the immune system and to protect the host. Grimble in "Malnutrition and the Immune Response", *Transactions of the Royal Society of Tropical Medicine and Hygiene* (1994) 88, 615–619, reports the influence of protein and amino acid intake on cytokine biology. The author also discusses the modulation of cytokine biology by fat and micronutrient intake.

Blood leukocytes represent only a small portion of the total number of leukocytes in the body, yet they provide an important representation of the state of activation of the immune system. It is known that acute stress induces large, rapid, and reversible changes in the distribution of peripheral blood leukocyte subpopulations. Leukocytes and other subpopulations of lymphocytes were examined by the inventors of this patent application to determine if nutritional supplementation could alter the response of the immune system to stress. The data reported below support the conclusion that the inventive composition is useful in preventing or reducing stress induced suppression of the immune system.

Convincing evidence has been accumulated to show that certain nutrients, particularly vitamins C and E, β-Carotene and calcium, are useful in the prevention and management of coronary heart disease, hypertension, certain cancers and osteoporosis. In addition, vitamins C, E and β-Carotene (antioxidant nutrients) seem to offer protection against exercise mediated free radical damage. Thus, it has been suggested that an antioxidant nutrient regimen should be made an integral part of any exercise program directed towards prevention/management of chronic disease and promotion of health. An excellent discussion of antioxidants and physical performance can be found in: (1) "Antioxidants in Infection" by Keuchs, *J. Nutr. Sci. Vitaminol.*, S23–S33 (1993); (2) Aruoma, "Free Radicals and Antioxidant Strategies in Sports", *J. Nutr. Biochem.*, 1994, vol. 5, pp. 370–380; and (3) Clarkson, "Antioxidants and Physical Performance", *Critical Reviews of Food Science and Nutrition*, 35(1&2):131–145 (1995).

A good example of physical and mental stress can be found in the military training exercises utilized by modern armies around the world. The military trainees experience increased incidence of infectious diseases as do populations of humans that are stressed by natural disasters, wartime refugee status and the like. A paper by Bernton, et al., "Adaptation to Chronic Stress in Military Trainees, *Ann NYAcad. Sci.*, Vol. 774 (217–231), 1995, reports the findings of studies investigating metabolic, cognitive, endocrinologic and immunologic adaptation in soldiers enrolled at the U.S. Army Ranger School during eight (8) weeks of extremely stressful training. The stress was both physical and emotional.

During the field training, the soldiers were provided only field rations. The ration provided fewer calories than those expended during the field exercise. As the ration provided fewer calories than those expended during the exercise, the soldier was in constant hunger and a progressive weight loss occurred during the exercise. Immune system suppression was evaluated by delayed type hypersensitivity by epicutaneous skin testing to seven (7) antigens. Significant suppression in both the mean number of positive skin tests and total millimeters of skin test induration was noted. Furthermore, it has been found in hospitalized patients that anergy as assessed by delayed type skin hypersensitivity indicates an increased risk of infection and mortality. See Christou NV, et al., "Two techniques of measurement of the delayed hypersensitivity skin test response for the assessment of bacterial host resistance." *World J. Surg.*, 1985;5:798–806 and Christou NV, et al., "The delayed hypersensitivity response and host resistance in surgical patients 20 years later." *Ann Surg.* 1995;222:534–461. These papers make no suggestion of a nutritional product that would successfully protect a stressed immune system from degradation.

U.S. Pat. No. 4,981,844 to Alexander, et al., discloses a method of improving the immune response in patients comprising the ingestion of a diet that provides 20–60 kilo calories per kg of patient body weight and wherein 20–80% of the calories are derived from linoleic acid. The Alexander, et al., patent also teaches the consumption of from 100–1000 IU per day of vitamin E.

U.S. Pat. No. 5,556,644 to Chandra discloses a multinutrient nutritional supplement designed to be effective in increasing immunity and decreasing the instances and severity of infection among the elderly. This patent specifically teaches the consumption of a nutritional supplement having recited levels of various vitamins and minerals. The patent more specifically teaches the consumption of the nutritional supplement by the elderly to improve their immunological status.

U.S. Pat. No. 5,444,054 to Garleb, et al., discloses a nutritional product for patients suffering from ulcerative colitis or inflammation of the colon. The nutritional product utilizes an oil blend containing specified fatty acids and a source of indigestible carbohydrate. The indigestible carbohydrate is disclosed as being metabolized to short-chain fatty acids by microorganisms present in the human colon.

U.S. Pat. No. 5,223,285 to DeMichele, et al., discloses a liquid nutritional product that contains a specific lipid blend for pulmonary patients. This patent discloses that the lipid should have a particular ratio of n-6 to n-3 fatty acids. Further, this reference describes a nutritional product containing quantities of nutrients having antioxidative properties in vivo. Examples of such antioxidative nutrients include β-Carotene, vitamin E, vitamin C, selenium and taurine.

U.S. Pat. No. 4,871,768 to Bistrian, et al., describes a dietary supplement that contains a structured glyceride comprising n-3 fatty acids and medium chain fatty acids. This patent describes synthetic triglycerides or structured lipids that provide a high energy fat source and fatty acids that assist in fighting infection. This patent also describes a method of minimizing the effects of infection and minimizing the effects of subsequent infection by administering a diet containing 10–80% by weight of an oily fraction comprising glycerol, fatty acids and combinations thereof wherein 50–90% of the fatty acids are caprylic acid, capric acid or mixtures thereof and 10–50% by weight of n-3 fatty acids. This reference teaches that the dietary supplement will not prevent the onset of infections, however, it will promote survival of infected patients. This patent fails to suggest that stress induced down regulation of the immune system can be lessened by a nutritional composition that comprises (1) a structured glyceride; and (2) an antioxidant system comprising at least vitamin E, vitamin C, selenium and β-Carotene.

WO 96/31457 (PCT GB 96/00828) to Horrobin, et al., describes structured lipids with two (2) or three (3) different fatty acids chosen from the twelve (12) essential fatty acids, oleic acid and other fatty acids containing 8–26 carbon atoms. The Horrobin structured lipids are suggested as pharmaceuticals for the treatment or prevention of disease in that abnormalities of the essential fatty acid metabolism have been identified.

U.S. Pat. No. 4,607,052 to Mendy, et al., describes triglycerides wherein specific polyunsaturated acyl fragments are present at the sn-2 position of the glycerol molecule. The structured lipids of Mendy, et al., are described as being useful for the treatment of lipid digestion problems, metabolic diseases, nutritional deficiencies, hypertension and in conditions where immune modulation is desired. There is no teaching nor suggestion in the Mendy, et al., patent that a structured glyceride, when combined with a specific antioxidant system, would be effective in reducing the immunosuppression typically seen in an animal subjected to stress.

WO 96/39869 to Schmitz, et al., discloses a health food product having various ingredients in discrete portions of a solid food product. One portion is taught to contain antioxidants while the second portion contains fat, protein, and carbohydrate.

The prior art fails to suggest or disclose a nutritional composition comprising a structured glyceride component and a unique antioxidant system that is effective in reducing or minimizing stressed induced immune system dysregulation or suppression. The inventive nutritional composition will sometimes hereinafter be referred to as an immunonutritional. The prior art also fails to suggest or disclose a method to reduce or prevent stress induced suppression of the immune system wherein the method comprises administration of a nutritional product comprising a structured glyceride component and an antioxidant system to a individual.

BRIEF DESCRIPTION OF THE DRAWINGS

To acquaint persons skilled in the art with the principles of the invention, a presently preferred embodiment illustrative of the invention follows with reference being made to the attached drawings forming a part of the specification and of which.

METHODOLOGY OF STUDIES DEPICTED IN DRAWINGS

Figure 1:
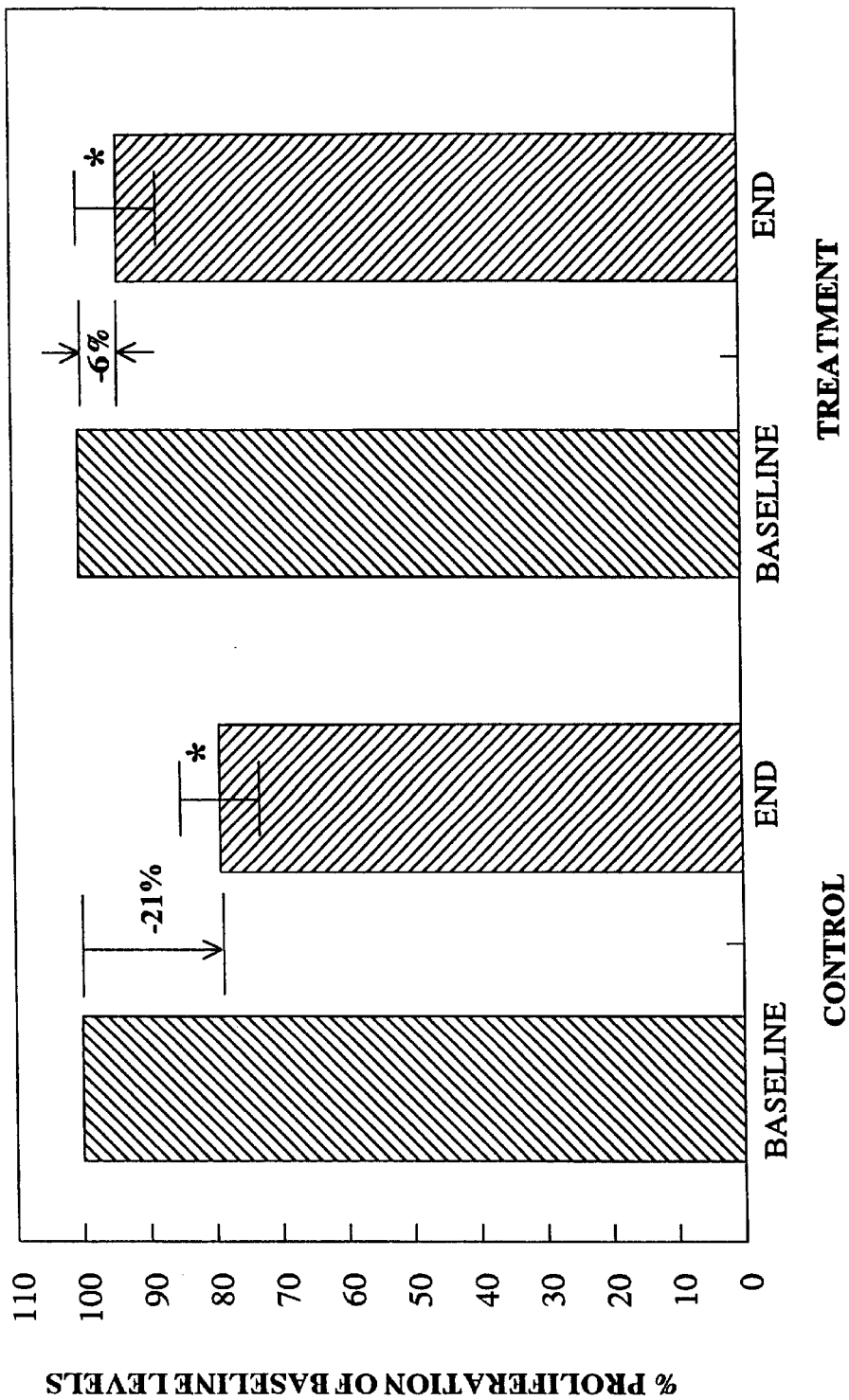
FIG. 1 is a chart of lymphocyte proliferation resulting from the data collected in Example 1.
Figure 3:
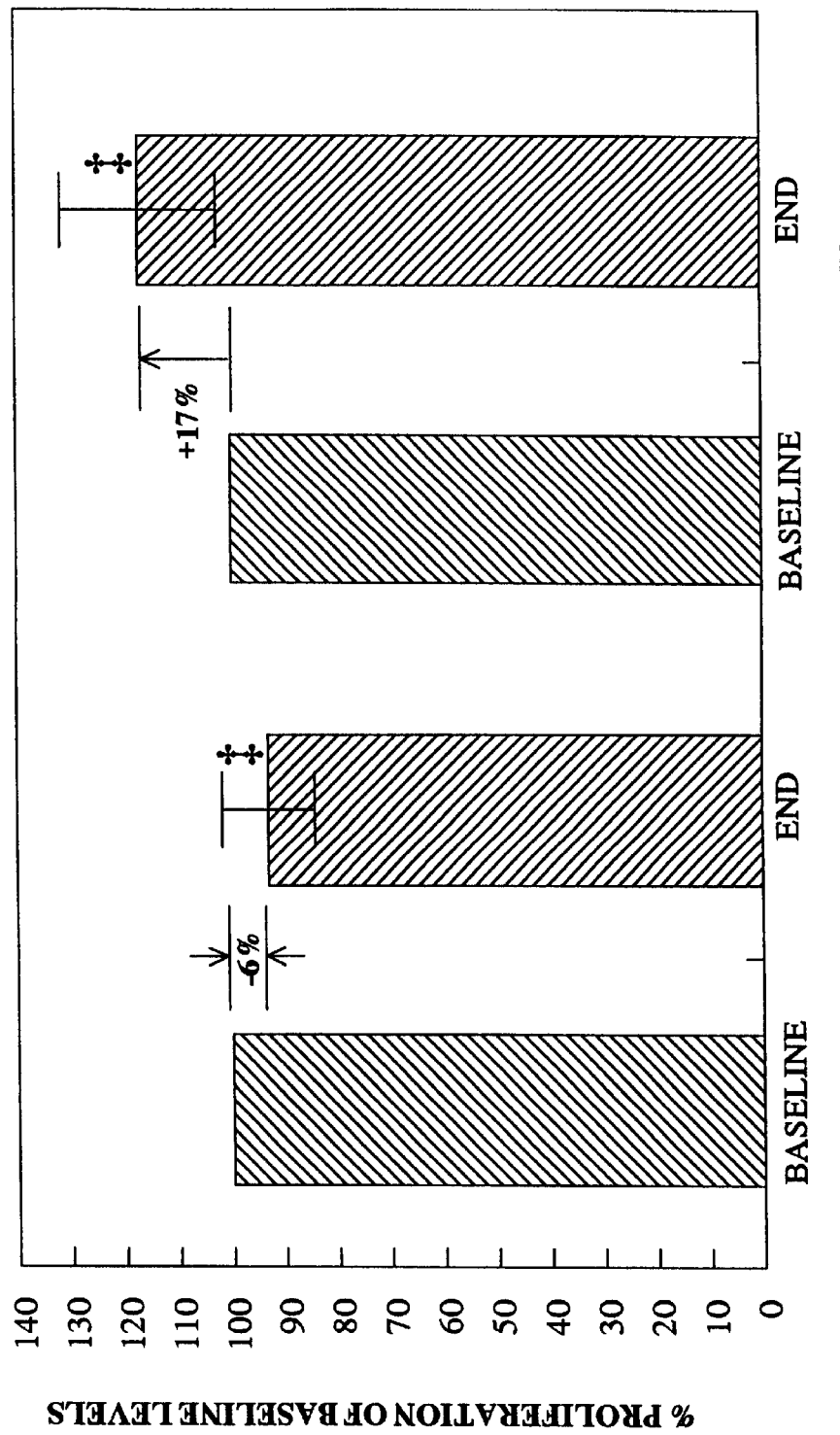
FIG. 3 is a graphical representation of changes in lymphocyte proliferation from baseline to end of study of soldiers consuming the Control beverage or beverage according to the invention as set forth in Example II.

In the figures that form a part of this specification, FIGS. 1 and 3 show lymphocyte proliferation of soldiers consuming control or antioxidant products. Blood was drawn (into sodium heparin vacutainer®—Becton Dickinson Co., Rutherfored, N.J.) at baseline and end of the study. Blood samples were obtained at the same time of day (0500) after the subjects had fasted except for water for 8 hours. Total blood cell counts were performed using a Coulter JT Blood Analyzer to determine white cell counts. Whole blood cultures were incubated in triplicate (5% $CO_2$, 95% humidified air at 370° C.) with a mitogen at optimal maximum mitogenic proliferative responsiveness of blood lymphocytes for 72 hours (as described by Kramer, et al., 1990; Bocchieri, et al., 1989). Mitogens included phytohemagglutinin for FIG. 1 (8 mg/mL, PHA—Sigma Chemical Co., St. Louis, Mo.) in cell culture media—complete RPMI 1640 and concanavalin A for FIG. 3 (10 mg/mL ConA—Pharmacia, Silver Spring, Md.) in cell culture media-complete PMI 1640. Cultures were pulsed with 1 mCi $^3$H-thimidine and cultured for an additional 18 hours. Cells were harvested and incorporation of labeled thymidine was detected in a beta liquid scintillation counter (Beckman LS 3801). The dpm per culture were then divided by lymphocyte cell number of the whole blood to obtain a dpm per cell. Each individual's baseline measurement was compared with the measurement at the end of the study.

References:

Bocchieri M H, Talle M A, Maltese L M, Ragucci I R, Hwang C C, Goldstein G A D. Whole blood culture for measuring mitogen induced T cell proliferation provides superior correlations with disease state and T cell phenotype in asymptomatic HIV-infected subjects. J Immunol Methods, 1995;181:233–43.

Kramer T R Praputpittaya K, Yuttabootr Y, Singkamani R, and Trakultivakrn M. Relationship between plasma zinc and cellular immunity to candida albicans in young females of Northern Thailand. Ann NY Acad Sci, 587:300, 1990.

Figure 2:
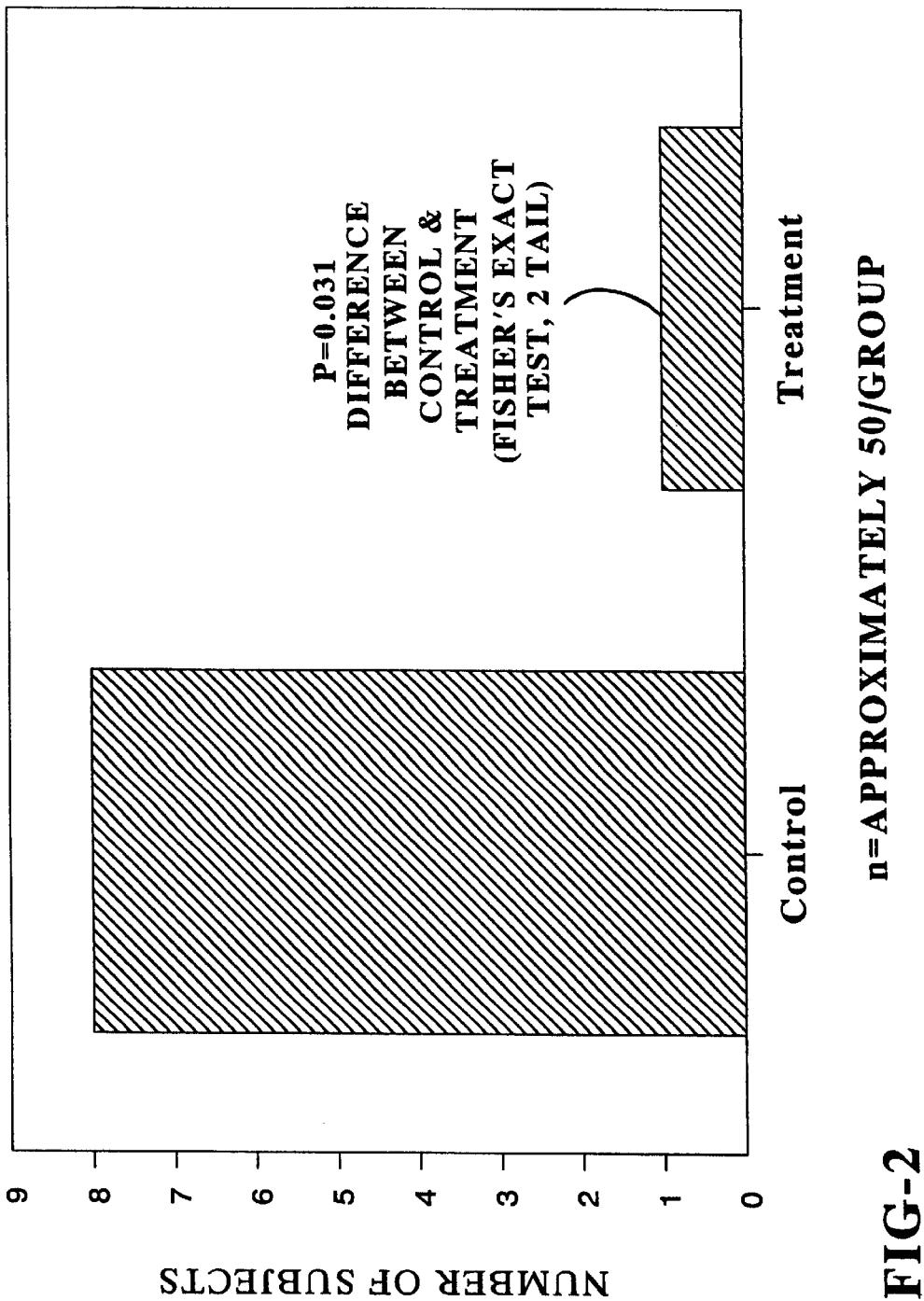
FIG. 2 is a graphical representation of the upper respiratory tract infection of soldiers consuming the Control beverage or treatment product from the data collected in Example II.

FIG. 2 represents upper respiratory infections of soldiers consuming the control and experimental products containing similar amount of energy and macronutrients, but differed in lipid composition (treatment contained structured lipid) and micronutrient (including antioxidant system) concentration. Determination was diagnosed by a military physician.

Figure 4:
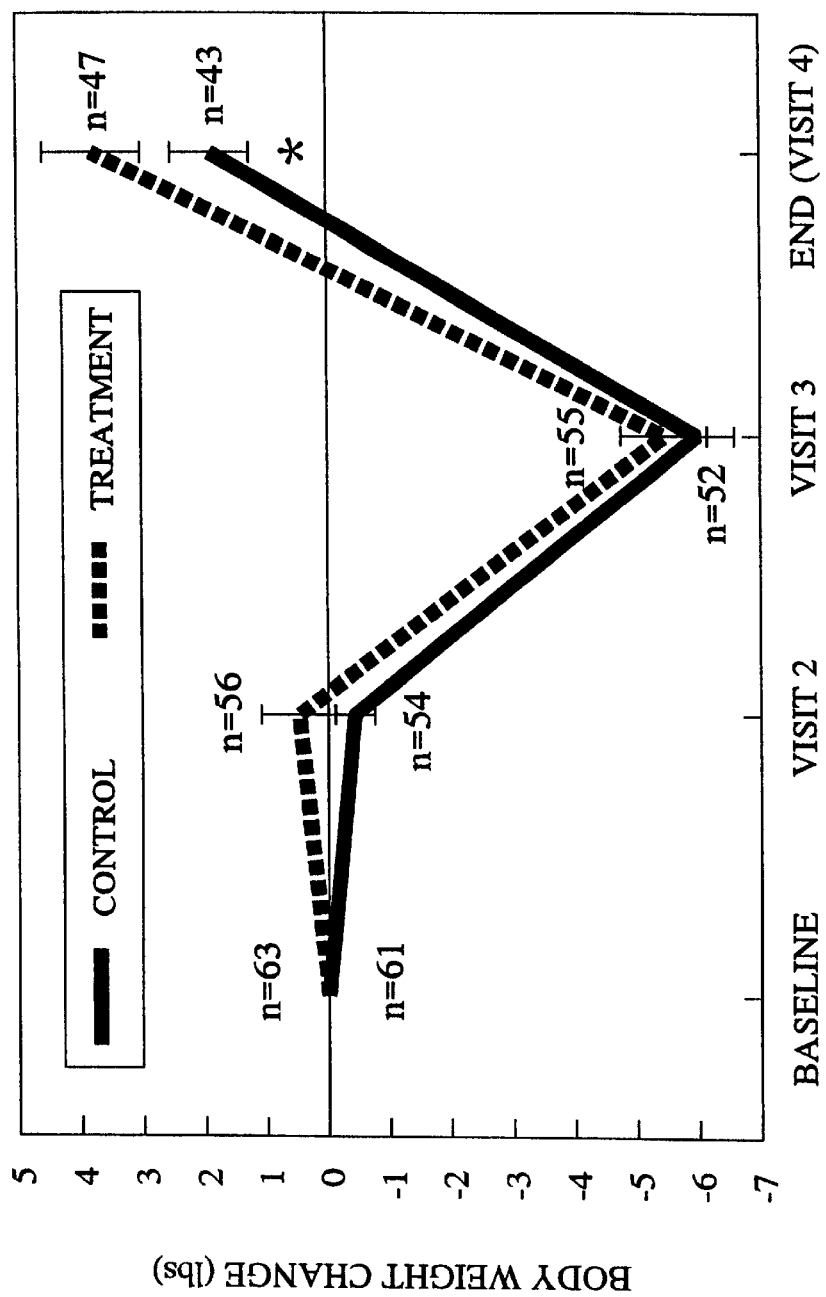
FIG. 4 is a graphical representation of changes in the body weight of the soldiers participating in Ranger training who consumed either a control bar or a bar according to the invention as described in Example 4.

FIG. 4 shows change in body weight that was measured at each blood sampling. Soldiers were measured without their boots using a calibrated digital electronic battery powered scale, accurate to 0.1 kg.

Figure 5:
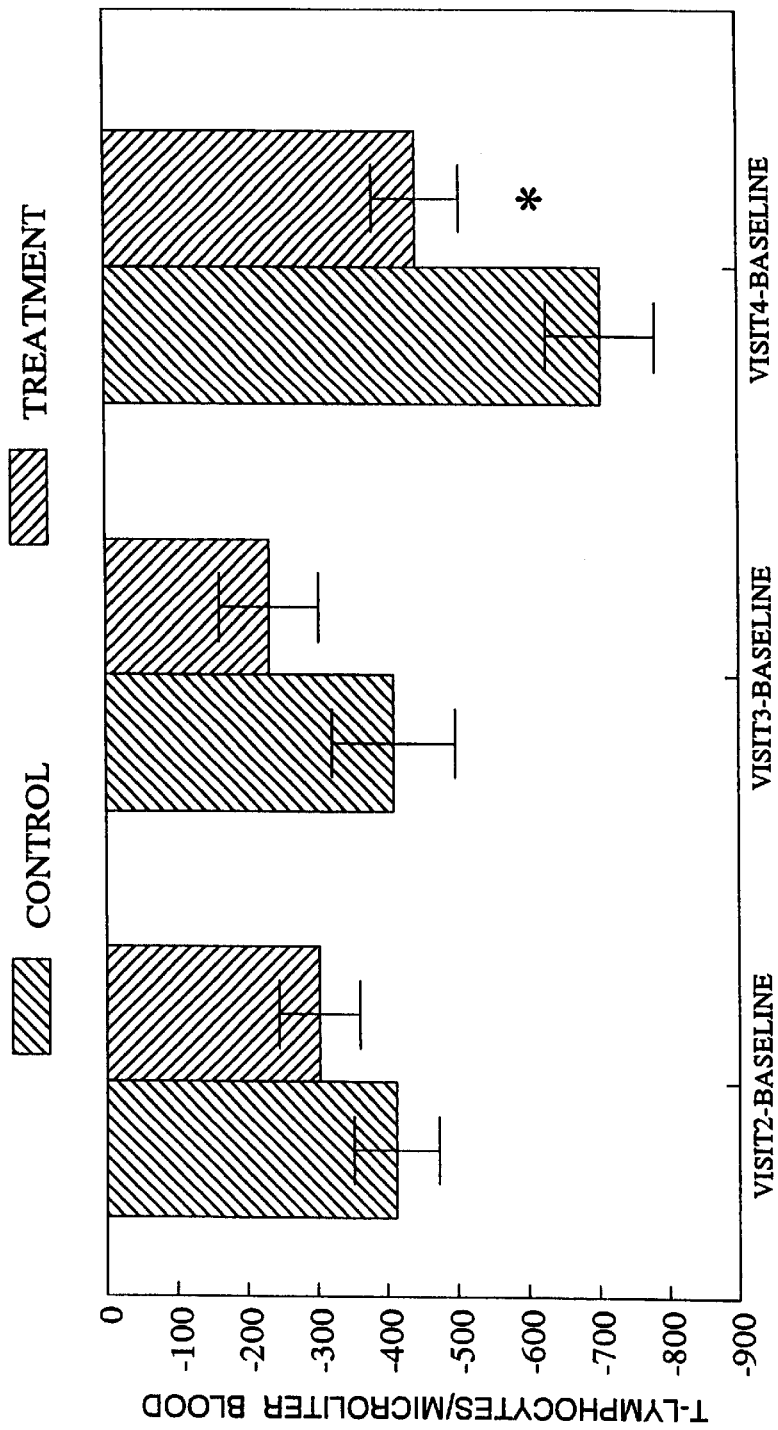
FIG. 5 is a graphical representation of the change in the number of T-lymphocytes of soldiers consuming either the control bar or a bar according to the invention as described in Example 4.
Figure 6:
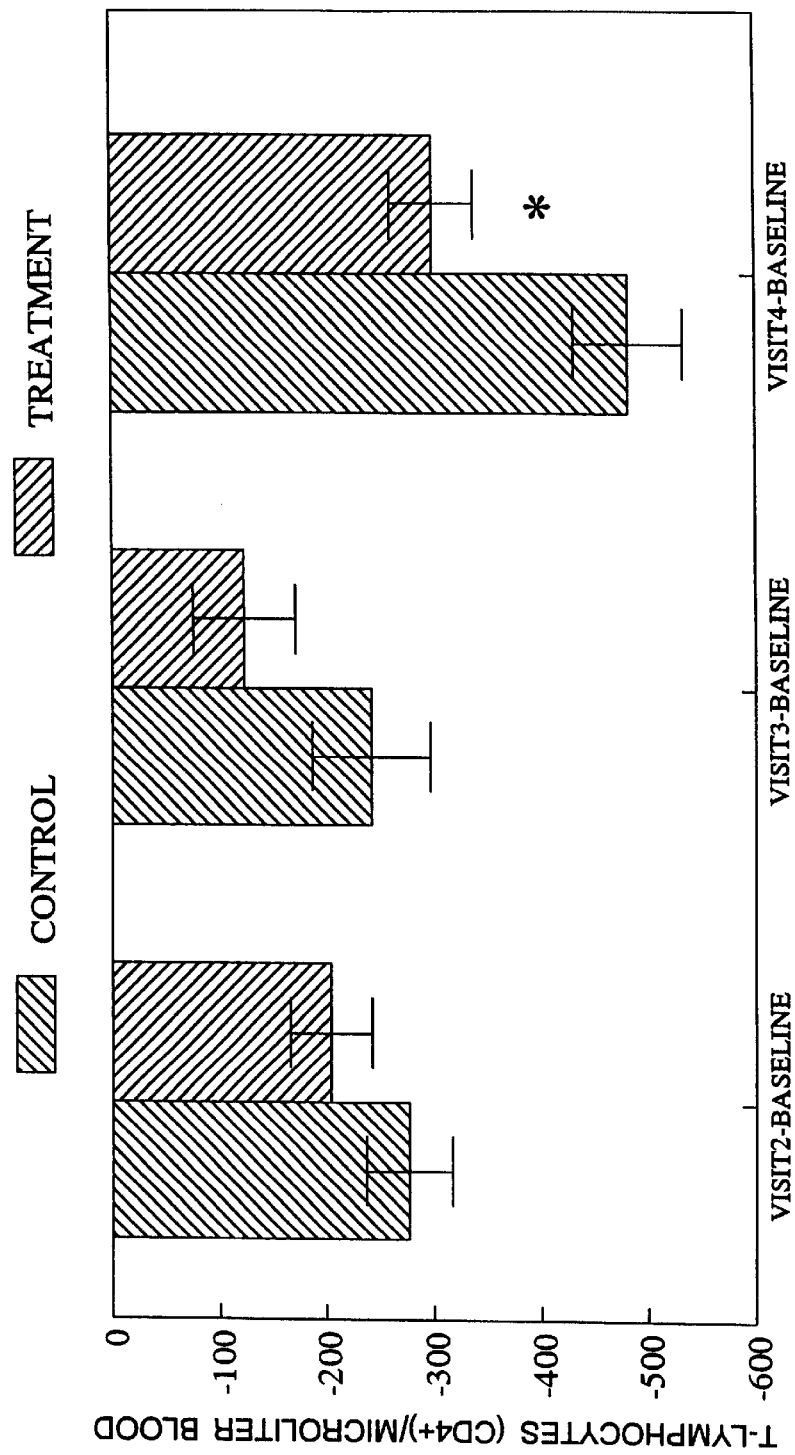
FIG. 6 is a graphical representation of the change in the number of T-lymphocytes (CD4+) of soldiers consuming either the control bar or a bar according to the invention as described in Example 4.
Figure 7:
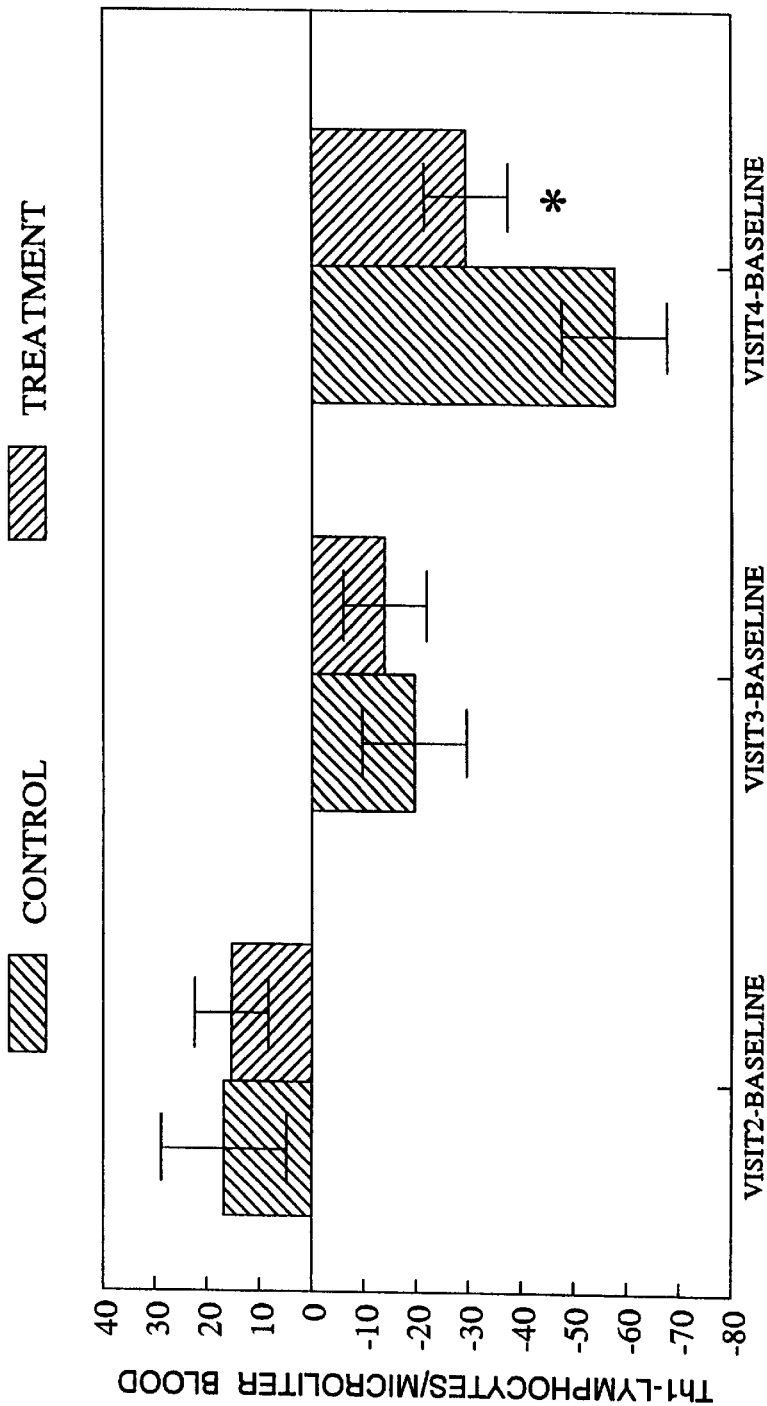
FIG. 7 is a graphical representation of the change in the number of TH1-lymphocytes of soldiers consuming either the control bar or a bar according to the invention as described in Example 4.

FIGS. 5–7 show changes in the number of lymphocytes of soldiers consuming control or treatment product of example 3. Blood was drawn as described above into sodium heparin vacutainer® (Becton Dickinson Co., Rutherford, N.J.) at four times points. Venous blood samples were obtained on all subjects on the same day and at the same time (between 10 pm and 1 am). Furthermore, the blood samples were processed exactly the same at each time point. Total blood cell counts and differential were performed using an Abbott Laboratories Cell Dyn® (North Chicago, Ill.). FIGS. 5 and 6 represent change (visit 2 from baseline, visit 3 from baseline, and visit 4 from baseline) in the subset of T-lymphocytes as analyzed by conventional flow cytometry or flow microfluorometry methods. In brief, whole blood samples were drawn and treated with a red blood cell lysine solution. The remaining cells were washed to remove cellular debris and incubated with monoclonal antibodies (ie. anti-CD3 and anti-CD4 antibodies) labeled with fluorochromes. Once the fluorochrome labeled antibodies were attached to specific cell populations they were washed and fixed. The labeled and unlabeled cells were then injected into the flow cytometer and individually illuminated by a laser. The cell numbers were calculated by using the percent of lymphocytes and specific subsets of lymphocytes as well as the total white blood cell counts. This technology allowed accurate and rapid evaluation of multiple properties of a singe cell or cellular populations. Analyses were performed on a minimum of 10,000 cells in a FACScan and Attractors software (Becton Dickinson, San Jose, Calif.). In FIG. 7, lymphocytes were processed and then stimulated for four hours with PMA and ionomycin. Cells were permeabolized and then exposed to antibodies directed towards cytokines produced by Th1 or Th2 lymphocytes. Change in the number of these specific CD4+ lymphocytes were determined by flow cytometry as described above. A two sample t-Test was used to compare the groups. The residuals obtained from fitting the model were examined with Shapiro-Wilk test for assessing if the residuals were normally distributed. Any parameters for which there was evidence that the residuals were not normally distributed (P<0.05) at one or more time point, they were analyzed with non parametric methods. This consisted of ranking the data and then analyzing the ranks with the Two Sample t-Test, in essence the Wilcoxon Rank Sum Test. Mean changes are presented with SEM, *P<0.05 and ‡P<0.10 difference between control and treatment.

SUMMARY OF THE INVENTION

In accordance with the present invention, it has been discovered that suppression of the immune system, which is typically associated with stress, can be prevented or decreased by the ingestion of antioxidants in conjunction with a structured glyceride component. Individuals undergoing stress have been found to have less responsive lymphocytes than a comparable individual who is not under stress. It has been shown that the combination of a structured glyceride component and antioxidants prevents, or significantly reduces, this reduction in the lymphocytes+ responsiveness. Additionally it has been demonstrated in clinical studies that stressed individuals who consume a structured glyceride component in conjunction with antioxidants had lower rates of infection, than a comparable control group that did not ingest this combination.

A further aspect of this invention is directed to pharmaceutical and nutritional compositions containing a structured glyceride component in combination with antioxidants. Another aspect of the invention is directed to a method for treating stress induced suppression of the immune system with one of the compositions described above. Other aspects and embodiments of the invention will become readily apparent to those skilled in the art.

The first component of the compositions or methods of this invention are the antioxidants. The specific antioxidants that produce this beneficial effect on the immune system are vitamin E, selenium, vitamin C, and β-Carotene. The specific amount of each antioxidant that should be ingested by the individual in order to prevent, or reduce, stress related immune suppression can vary widely depending upon the individuals age, weight, sex, or the presence of other underlying disease states. However, listed below in Table I are guidelines for the amount of each antioxidant that may be administered per dose, to the stressed individual. The amounts listed below are merely being presented in order to further illustrate and exemplify the invention. They should not be construed as limiting the invention in any manner. Further, they are being presented in tabular form to aid the reader, and this description should be considered as encompassing a combination in which one antioxidant is present at the suggested minimum level, while another is present at the most preferred level, or any combination thereof.

DOSAGE GUIDELINES FOR ANTIOXIDANTS

| Antioxidant | Suggested Minimum | More Preferred | Most Preferred |
|---|---|---|---|
| Vitamin C | at least 250 mg | 0.5–5.0 gm | 1–3 gm |
| Vitamin E | at least 200 IU | 200–1000 IU | 200–600 IU |
| β-Carotene | at least 7.5 mg | 7.5–50 mg | 15–35 mg |
| Selenium | at least 50 ug | 50–400 ug | 100–200 ug |

The second component of the compositions or methods of this invention is the structured glyceride component. The structured glyceride component utilized in this invention are typically triglycerides. A structured triglyceride component useful in this invention comprises 33 to 70 wt. % acyl moieties of medium chain length (i.e. 4 to 12 carbon atoms). More preferably the medium acyl chains comprise 45 to 70 wt. %, and most preferably 50 to 65 wt. %. At all weight percents, the length of the medium acyl chains is preferably 4 to 12 carbon atoms, more preferably 6 to 12, most preferably 8 to 10 carbon atoms. The 30 to 67 wt. % remainder of the structured triglyceride is typically a long chain (13–22 carbon atoms) acyl moiety. More preferably the long acyl chains comprise 30 to 55 wt. %, most preferably 35 to 50 wt. %. Preferably, said long chain acyl moiety at all weight percents comprises a long chain polyunsaturated fatty acid residue. The structured glyceride component is preferably characterized as comprising at least 40% (W/W) of a species with equivalent carbon number (ECN) of greater than 30 to less than 48, more preferably ECN of about 32 to about 42.

The amount of the structured glyceride component that should administered can also vary widely depending upon the individual's age, weight, sex, or the presence of other underlying disease conditions. However, as a general guideline, an individual will typically be administered per dose at least 1 gram of a structured glyceride component, more preferably from 1–100 gm and most preferably from 10–50 gm of the structured glyceride component.

In order to produce the beneficial effects on the immune system of a stressed individual, the combination of a structured glyceride component and the antioxidants should be administered at least once per day and more preferably twice per day. This combination has been shown to be highly effective in reducing or preventing immune system dysregulation as a result of stress. The term "dysregulation" means that the immune system is functioning in a manner that is less effective from that found in the typical or normal state. An animal experiencing dysregulation of its immune system is more susceptible to disease and less able to fight infections.

DETAILED DESCRIPTION OF THE INVENTION

According to this invention, selected antioxidants are used in conjunction with a structured glyceride component. By "in conjunction with" we mean that the antioxidants compounds are administered to said individual within one hour of administration of the structured glyceride component. More preferably, the antioxidants are administered at the same time as the structured glyceride component, most preferably admixed in the same composition, such as enteral nutritionals, nutritional supplements, tablets, pills, capsules, suppositories, sprays, lozenges, drops, lotions, ointments, microcapsules and liposomes.

The term "edible oil" means any oil derived from plants, animals, single celled organisms and the like that can be eaten by a mammal and used as a source of nutrition. The term "lipid" denotes a heterogeneous group of substances associated with living systems that have the common property of being insoluble in water and soluble in non-polar solvents such as hydrocarbons and alcohols.

The term "structured lipid" generally refers to an oil or fat that contains specific fatty acyl residues in a specific position on the glycerol backbone. As used in this invention, a "structured glyceride component" refers to a glyceride mixture characterized in that it may contain mono-, di, and triglycerides, more typically di and triglycerides, ideally a higher percentage of triglycerides. At least 40% of the triglyceride species have about 33–70 wt. % of acyl moieties having 4 to 12 carbon atoms, about 30–67 wt % of acyl moieties having more than 12 carbon atoms and an equivalent carbon number of greater than 30 to less than 48.

A glyceride is an ester of glycerol (1,2,3-propanetriol) with acyl radicals of fatty acids and is also known as an acylglycerol. If only one position of the glycerol molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. A glyceride is called "simple" if all esterified positions contain the same fatty acid; or "mixed" if different fatty acids are involved. The carbons of the glycerol backbone are designated sn-1, sn-2 and sn-3, with sn-2 being in the middle and sn-1 and sn-3 being the ends of the glycerol.

Naturally occurring oils and fats consist largely of triglycerides wherein the 3 fatty acyl residues may or may not be identical. The term "long chain triglycerides (LCT)" means both a simple and mixed triglyceride containing fatty acids with more than 12 carbon atoms (long chain fatty acids—"LCFA"), whereas the term "medium chain triglycerides (MCT)" means both a simple and mixed triglyceride containing fatty acids with 4 to 12 carbon atoms.

The term "ECN" or "equivalent carbon number" means the sum of the number of carbon atoms in the acyl chains of a glyceride molecule. For example, tripalmitin (tripalmitic glycerol), which is a simple triglyceride containing 3 acyl radicals of 16 carbon atoms, has an ECN of 3×16=48. Conversely, a triglyceride with an ECN=40 may have "mixed" acyl chain lengths of 8, 16 and 16; 10, 14 and 16; 8, 14 and 18, etc. Naturally occurring oils are frequently "mixed" with respect to specific fatty acids, but tend not to contain LCFAs and MCFAs on the same glycerol backbone. Thus, triacylglycerols with ECN's of 24–30 typically contain predominately medium chain fatty acids; while triacylglycerols with ECN's of greater than 43 typically contain predominantly long chain fatty acids. Triacylglycerols having ECN's of 32–42 typically contain one or two MCFA in combination with one or two LCFA's to "fill" the triglyceride. Triacylglycerols with ECN's in the range of greater than 30 to less than 48 typically represent mixed triacylglycerol species that are essentially unique to the structured triglyceride and are absent from or are present in significantly lower concentrations in physical mixtures.

The terms "wt. %" or "weight percent" means the ratio of the mass of the recited component to the mass of the specified ingredient or entire composition multiplied by 100. For example, "a triglyceride comprising 40 wt. % acyl moieties of 10 carbon atoms" means that 100 gms of the triglyceride oil consists of 40 gms of 10 carbon atoms acyl radicals and 60 gms of other components, including other acyl radicals and the glycerol backbone.

Many of the properties of food lipids can be accounted for directly in terms of their component fatty acids. The fatty acids that occur in foodstuffs usually contain an even number of carbon atoms in an unbranched chain, e.g., lauric or dodecanoic acid. Besides the saturated fatty acids, of which lauric acid is an example, fatty acids may have 1, 2 or sometimes up to 6 double bonds and are, therefore, unsaturated. The number and position of double bonds in fatty acids are designated by a convention of nomenclature typically understood by the organic chemist. For example, arachidonic acid ("M" or "ARA") has a chain length of 20 carbons and 4 double bonds beginning at the sixth carbon from the methyl end. As a result, it is referred to as "20:4 n-6". Similarly, docosahexaenoic acid ("DHA") has a chain length of 22 carbons with 6 double bonds beginning with the third carbon from the methyl end and is thus designated "22:6 n-3".

The term "NAS-NRC RDA" means the National Academy of Sciences-Nutrition Research Council Recommended Dietary Allowances.

For the purposes of the disclosure contained within the this document, the term "antioxidants" refers to the following four substances: vitamin C, vitamin E, selenium, and β-Carotene.

The term "β-Carotene" means the carotenoid precursor of vitamin A found in plants. Because there are various compounds that have vitamin A activity, sources are usually expressed as retinol equivalents (RE). The conversion for β-Carotene is 1 RE equals 6 μg of all-trans β-Carotene. Therefore, the 15 mg of β-Carotene equals 2500 RE. The data on carotenoid content of foods are incomplete so it is not possible to state precisely what percentage of vitamin A activity in the diet is contributed by carotenoids. Using available food composition data, the United States Department of Agriculture found the average daily vitamin A intake of adult men to be 1419 RE. The NAS-NRC RDA for adult males has been set at 1000 RE per day. Signs of Vitamin A toxicity usually appear only with sustained daily intakes, including both foods and supplements, exceeding 15,000 RE. Contrasted with retinol, carotenoids, even when ingested in very large amounts for weeks to years, are not known to be toxic. The main reasons for their lack of toxicity are: markedly reduced efficiency of absorption at high doses, and relatively limited conversion to vitamin A in the intestine, liver and other organs. β-Carotene is a vitamin A source; however, it is not toxic like vitamin A when given in very high doses. β-Carotene is found in yellow, orange, and dark leafy green vegetables and seems to be a unique antioxidant.

The term "vitamin E" means a group of tocopherols that have the designations: α-, β-, δ- and -γ, that differ only in the number and position of methyl groups on the ring. The most active form of vitamin E, α-tocopherol, is also the most widely distributed in nature. When α-tocopherol was first synthesized, the synthetic material was found to have a slightly lower biological activity than the α-tocopherol from plants. Because of this phenomena, the natural occurring form has been designated RRR-α-tocopherol. For dietary purposes, vitamin E activity is expressed as RRR-α-tocopherol equivalents (-TEs). One α-TE is the activity of 1 mg of RRR-α-tocopherol. One mg of RRR-α-tocopherol is equivalent to 1.49 IU of vitamin E. The NAS-NRC RDA has been established at 10 mg -TE per day for adult males. Analyses of balanced diets indicate that the average daily intakes of α-TE range from 7 to 11 mg. Adults tolerate oral doses of 100 to 800 mg/day without symptoms or biochemical evidence of toxicity.

The term "vitamin C" means ascorbic acid. Ascorbic acid intake for adult males between the ages of 20 and 29 years was found to average 121 mg per day (U.S. Dept. of Health and Human Services, 1994). The NAS-NRC RDA for ascorbic acid has been set at 60 mg for adult males. Many people habitually ingest 1000 mg per day of ascorbic acid without developing apparent toxic manifestations.

The term "selenium" means any chemical compound that provides biologically available selenium. Analyses of food intake in the United States indicate that the overall adult mean dietary selenium intake was 108 μg per day between 1974 and 1982. The NAS-NRC RDA for selenium has been established at 70 μg per day for adult males. The level of dietary selenium exposure needed to cause chronic poisoning in humans is not known with certainty. However, approximately 5 mg per day from foods resulted in fingernail changes and hair loss in a seleniferous zone of China.

Any reference in this application to a quantity of selenium, or any other mineral, including copper, should be understood as referring to the elemental amount of the mineral and not any associated anion. One skilled in the art can readily calculate how much of a mineral salt, salt or mineral complex should be added to the nutritional or pharmaceutical product in order to deliver the desired amount of the elemental mineral.

"Indigestible oligosaccharide" refers to a carbohydrate that is resistant to endogenous digestion in the human upper digestive tract. FOS are indigestible oligosaccharides that are members of the inulin subclass of fructosans; polymers composed of fructose residues. Specifically, inulins are glucofructosans, carbohydrate polymers consisting of a chain of fructose residues linked by (2→1)-β-glycosidic bonds and usually having a single D-glycosyl residue lined (1→2)-α to the first fructose molecule. FOS can be produced enzymatically through chemical techniques or by extraction from natural substances. FOS occur in nature in many kinds of plants including onions, garlic, shallots, artichokes, wheat, rye, bananas, asparagus and tomatoes that are commonly part of a human diet. An enzymatic method of producing FOS industrially is taught in U.S. Pat. No. 4,681,771 to Adachi, et al., that comprises reacting sucrose in the presence of a fructosyltransferase to obtain GF2, GF3, GF4 and GF5. The source for the enzyme fructosyltransferase could be a fungus such as *Aspergillus niger* or a vegetable.

The term "FOS" means fructooligosaccharides, FOS are natural substances composed primarily of fructose molecules. They belong to a group of carbohydrates that occur in many different plants. FOS are indigestible oligosaccharides that pass through the small intestine without being digested, reaching the large intestine where they are selectively fermented by certain microorganisms. FOS can be utilized efficiently by lactobacilli and bifidobacteria, a species of bacteria that are beneficial for human health. Selective fermentation of FOS by bifidobacteria leads to an increase in the presence of these bacteria and to the production of acetic acid and lactic acid, resulting in a lower pH in the digestive tract and providing a means to prevent the overgrowth of harmful bacteria like *E. coli, Clostridium perfringes* and *Clostridium difficile*. Indigestible oligosaccharides such as FOS may be added to the immunonutritionals according to the invention to create an environment in the gastrointestinal tract that is not conducive to the growth of microbial pathogens and to enhance the immunosupportive properties of the inventive immunonutritionals.

Animal toxicity studies have shown no evidence of toxicity, mutagenicity or carcinogenic effects due to FOS and indigestible oligosaccharides. A therapeutically effective amount of FOS or indigestible oligosaccharide in the present invention can range from 1.0 to about 10 gms per day. More preferably, the amount of FOS consumed is about 5.0 to 10.0 gms per day, with a most preferred level of about 8.0 to 10 gms per day. The presence of indigestible oligosaccharides or FOS is optional in the immunonutritionals of the instant invention.

As used in this application, dietary fiber is understood to be all of the components of food that are not broken down by enzymes in the human digestive tract to produce small molecular compounds, and are therefore not absorbed. Examples of dietary fibers that may be utilized in addition to FOS include soy polysaccharide, oat hull fiber, gum arabic, sodium carboxymethylcellulose, guar gum, pectin, corn bran, etc. More preferably any dietary fibers utilized in the compositions will be an admixture of insoluble fibers, soluble fermentable and soluble nonfermentable fibers as described in U.S. Pat. No. 5,104,677. The disclosure of the '677 patent is hereby incorporated by reference. Any of the nutritional or pharmaceutical compositions of the instant invention may optionally contain dietary fibers.

The antioxidants utilized in the nutritional and pharmaceutical compositions of this invention are all well known in the art. They are available commercially from numerous sources well known to those skilled in the art.

In addition to antioxidants, all of the nutritional and pharmaceutical compositions of this invention contain a structured glyceride component, of at least 33 wt. % randomly esterified MCFA. The remainder of the fatty acid moieties are typically LCFA. The source of the MCT and LCT used to prepare the structured glyceride component is not critical. Typical sources of MCT such as fractionated coconut oil and fractionated palm kernel oils are known to those skilled in the art. Sources of LCFA include the oils derived from borage, black currant seed, corn, coconut, canola, soybean, marine oils, fungal oils, safflower, high oleic safflower, sunflower, high oleic sunflower, olive, evening primrose, cottonseed, rice bran, grapeseed, flaxseed, butterfat, garlic, peanuts, almonds, walnuts, wheat germ, egg, sesame, lard, tallow and mutton.

In a more preferred embodiment, the structured glyceride component of the invention also contains a long chain polyunsaturated fatty acid (hereinafter "LCPUFA") such as the n-6, n-9 and/or n-3 long chain fatty acids. Known sources of LCPUFA include fish or marine oil, egg yolk lipid, single cell oils (e.g., algal oils and fungal oils), it being understood in the art that some sources are better than others for achieving higher amounts of a specific LCPUFA. Other edible, semi-purified or purified sources of LCPUFA will be evident to persons skilled in the art. For example, new sources of LCPUFAs may be developed through the genetic manipulation of vegetables and oil bearing plants. The use of such recombinant oils are also contemplated in the present invention.

The structured glycerides useful in the present invention contain both MCFA and LCFA. The structured tryglycerides useful in this invention are chemically distinct and offer unique advantages from the starting materials from which they are derived. One aspect of the present invention resides in the discovery that structured triglycerides that contain a certain mixture of MCFA and LCFA are subject to rapid hydrolysis and absorption in comparison to LCT's. In addition, the structured triglycerides of this invention are primarily absorbed and transported through the lymphatic system as opposed to the hepatic route.

In native fats and oils, the various fatty acids are esterified through one of the three hydroxy groups of the glycerol molecule in an ordered pattern that is characteristic of the particular fat or oil. In general, the naturally occurring, long chain, saturated fatty acids (e.g., $C_{16}$–$C_{18}$) are predominantly at the sn-1 and sn-3 positions, while the mono- and polyunsaturated fatty acids are at the sn-2 or middle position of the triglyceride molecule. There are only a small number of naturally-occurring "simple triglycerides", for example, tripalmitin ($C_{16}$), triolein ($C_{18}$) and the like.

The structured glyceride component of this invention will predominantly contain triglycerides, 50% by weight or more, frequently about 90% by weight. Of these triglycerides (whatever their proportion) at least 40% by weight have an ECN greater than 30 and less than 48. More preferably, the structured glyceride component will contain at least 60% by weight the ECN greater than 30 and less than 48 species, most preferably at least 60% by weight the ECN of about 32 to about 42.

The structured glycerides of this invention may be prepared by any procedure commonly used to make structured lipids. For example, an interesterification or transesterification reaction made by mixing oils, or selective fractions of the oils, in stoichiometric proportions and then causing the transesterification reaction to proceed using catalysts or enzymes could be used. In addition, one skilled in the art could genetically engineer the oil bearing plants to produce the specific structured glycerides described in this invention. Although a standard transesterfication procedure may result in a component mixture containing the structured glycerides of the invention along with other oils, such a component mixture is intended to be included within the claims.

It is possible to source MCT oils as starting materials to prepare the structured lipids useful in this invention. MCT oils, such as fractionated coconut oil and fractionated palm kernel oils, are obtained by the hydrolysis of coconut and palm kernel oils and the distillation of the fatty acids. The fatty acids are then re-esterified to the glycerol molecules to obtain the MCT oil.

The chemical interesterification process used for the preparation of the structured triglycerides in the following examples is according to the teachings found in the "Oils and Fats Manual, A Comprehensive Treatise", Vol. 2, Chapter 11, *Transformation of Fat for Use in Food Products*, pgs. 923–925, the entire teaching of which is hereby incorporated by reference. Chemical interesterification, also called co-randomization (since it alters the non-random distribution of nature) may be accomplished by heating a mixture of oils for a short period of time (e.g. from 0.5 to 4 hours, preferably 0.5 to 2 hours at temperatures of 100–140° C., preferably 110–130° C.) in the presence of a catalyst such as sodium methylate or sodium methoxide (e.g. range from 0.05 to 0.5% by wt., more preferably from 0.1 to 0.3% by wt.) The fatty acids leave their natural position on the triglyceride and rearrange in a random fashion (presumably equally on each of the three positions). Thus, about one third of each individual fatty acid will re-esterify at the sn-1 position, about one third on sn-2 and about one third on sn-3.

As noted above, it is possible to prevent or reduce stress induced suppression of the immune system by separately administering the antioxidants and the structured glyceride component. Any such separate administration should be considered as part of the invention. However, it is much more convenient for the individual if the antioxidants and the structured glyceride component are administered together in a single composition. This composition can be administered in the form of a nutritional product such as, for example, an enteral formula or concentrate. Other nutritional products or food products include bars, puddings, gels, confectioneries, such as candies, gums, lozenges and the like. The antioxidant and structured glyceride component may also be administered as a pharmaceutical composition. Examples of suitable pharmaceutical compositions include tablets, capsules, suspensions, emulsions, solutions, etc.

A typical nutritional composition of the present invention will contain edible macronutrients, vitamins and minerals in amounts desired for a particular use. The amounts of such ingredients will vary depending on whether the formulation is intended for use with normal, healthy individuals temporarily exposed to stress, or to subjects having specialized needs due to certain chronic or acute disease states (e.g., metabolic disorders). It will be understood by persons skilled in the art that the components utilized in a nutritional formulation of the present invention are of semi-purified or purified origin. By semi-purified or purified is meant a material that has been prepared by purification of a natural material or by synthesis. These techniques are well known in the art (See, e.g., Code of Federal Regulations for Food Ingredients and Food Processing; Recommended Dietary Allowances, 10th Ed., National Academy Press, Washington D.C., 1989).

In a preferred embodiment, a nutritional formulation of the present invention is a liquid enteral nutritional product for a mammal, including humans such as adults, children, juveniles and infants. Accordingly in a further aspect of the invention, a nutritional formulation is provided that is suitable for feeding adults, who are experiencing stress. The formula comprises, in addition to the antioxidants and a structured glyceride component; macronutrients, vitamins and minerals in amounts designed to provide the daily nutritional requirements of adults.

The macronutritional components include edible fats, carbohydrates and proteins. Exemplary edible fats are coconut oil, soy oil, and mono- and diglycerides. Exemplary carbohydrates are glucose, edible lactose and hydrolyzed cornstarch. A typical protein source would be soy protein, electrodialysed whey or electrodialysed skim milk or milk whey, or the hydrolysates of these proteins, although other protein sources are also available and may be used. These macronutrients would be added in the form of commonly accepted nutritional compounds in amount equivalent to those present in human milk on an energy basis, i.e., on a per calorie basis.

Although not intended to limit the invention in any manner, but to merely serve as a general guideline, a liquid nutritional formula of this invention will typically provide the following caloric distribution. The protein system will typically provide from about 5% to about 25% of total calories, more preferably from about 10% to about 20% of total calories. The lipid system will provide from about 5 to about 50% of total calories, and more preferably from about 20% to about 40% of total calories, including the structured glyceride. Typically about 1040% of total calories will be provided by the structured lipid and more preferably 15–25%. The carbohydrate system will typically provide from about 20% to about 90% of total calories, more preferably from about 30% to about 60% of total calories.

Methods for formulating liquid and enteral nutritional formulas are well known in the art and are described in detail in the examples.

The enteral formula can be sterilized and subsequently utilized on a ready-to-feed (RTF) basis or stored in a concentrated liquid or a powder. The powder can be prepared by spray drying the enteral formula prepared as indicated above, and the formula can be reconstituted by rehydrating the concentrate. Adult and infant nutritional formulas are well known in the art and commercially available (e.g., Similac®, Ensure®, Jevity® and Alimentum® from Ross Products Division, Abbott Laboratories).

The energy density of the nutritional composition when in liquid form, can typically range from about 0.3 to 2 cal per ml. When in solid or powdered form, the nutritional supplement can contain from about 1.0 to more than 7 Kcals per gm. In general, the osmolality of a liquid product should be less than 700 mOsm and more preferably less than 660 mOsm.

When the structured glyceride component is incorporated into a nutritional composition, it will often be present in admixture with lipids, including naturally occurring glycerides, including triglycerides( i.e., non-structured glycerides). The presence of the non-structured glyceride will not have a detrimental effect on the present invention, provided that the structured glyceride component is present in an amount sufficient to have its beneficial effects on the stressed immune system. These amounts have been described above. In such a typical nutritional product, the structured glyceride component will comprise at least 20 w/w % of the total lipids contained within the product, more preferably at least 50 w/w %, and most preferably about 80 w/w %.

The nutritional formula would typically include vitamins and minerals, in addition to the antioxidants, in order to help the individual ingest the minimum daily requirements for these substances. In addition to the antioxidants listed above, it may also be desirable to supplement the nutritional composition with zinc, copper, and folic acid. It is believed that these substances will also provide a boost to the stressed immune system and thus will provide further benefits to the individual. If zinc is utilized, the typical dose will be at least 12.5 mg, more preferably 25–200 mg, and most preferably 50–150 mg. If copper is utilized the dose is typically at least 0.8 mg, more preferably 1.6–5.0 mg and most preferably 2–4 mg. If folic acid is utilized the dose is typically at least 100 ug, more preferably 200–600 ug, and most preferably 300–500 ug. These doses should be provided at least once per day and more preferably twice per day. The presence of zinc, copper or folic acid is optional and is not required in order to gain the beneficial effects on immune suppression. Likewise a pharmaceutical composition can be supplemented with these same substances as well.

In a more preferred embodiment, the immunonutritional contains, in addition to the antioxidant system and the structured glyceride component, a source of carbohydrate wherein at least 5 weight % of said carbohydrate is an indigestible oligosaccharide. In yet a more preferred embodiment, the nutritional composition additionally contains protein, taurine and carnitine.

In addition to enteral formulae, another preferred nutritional composition is one in solid form. Such solid forms include bars, cookies, crackers, etc. Such compositions are preferred by certain consumers. The solid compositions can be easier to transport due to their lighter weight. Some consumers prefer the tactile sensations associated with chewing and thus these solid forms expand the number of individuals who may receive the beneficial effects associated with the present invention.

Initial attempts to prepare these solid nutritional compositions were associated with difficulties. As noted above, the invention is the discovery that a structured lipid, in combination with certain antioxidants, reduces the suppression of the immune system that is associated with stress. Due to the requirement that the compositions contain substantial quantities of structured lipids, certain complications were encountered that negatively impacted the stability of the compositions, their palatibility to the consumer and their efficicacy in reducing suppression of the immune system.

Initially attempts were made to prepare bars containing effective amounts of the structured lipid and the antioxidants. These initial attempts were gross failures. Within minutes of preparing the core of the bar, lipid began to ooze from the core. Such bar cores were not processed, since hypothetically any such bar would be considered highly undesirable by test subjects. Further, due to the leaching of the lipid, it would be impossible to determine how much structured lipid the patient actually consumed and how much was lost. A leaching lipid would also tended to destroy the physical integrity of the bar. It is believed that this decrease in integrity would have a negative impact upon the stability of the ingredients of the bar. The ingredients would be exposed to additional oxygen and thus to a greater risk of oxidative degradation. It is believed that such bars would have unacceptably short shelf life's( ie. far less than the desired 12 month shelf life).

Through additional experimentation, the inventors developed bars that were no longer susceptible to this leaching problem. These new bars did not exhibit any leaching after a test period of at least 24 months . The solution to this leaching problem was to incorporate certain proteins into the matrix of the bar (or any other solid compostion). The leaching problem can also be improved by incorporating certain carbohydrates into the solid matrix as well.

Accordingly it has been discovered that solid nutritional compositions incorporating structured lipids can be prepared that will not leach the structured lipid. The solution to the problem is to incorporate soy proteins into the composition. The amount of soy protein that will produce this beneficial effect can vary widely. However incorporating from about 4 to about 20 w/w % (based upon the total weight of the solid nutritional), and more preferably from about 7 to about 9 w/w % of soy protein will minimize the leaching problem. Soy proteins from Protein Technologies, Inc. are currently utilized. If desired other protein sources may be incorporated into the bars as well.

Further beneficial effects can be produced by incorporating the emulsifier, lecithin, into the composition. The amount utilized can vary widely, but will typically range from about 0.4 to about 2 w/w % and more preferably about 0.8 to about 0.9 w/w % (based upon the total weight of the composition). Additional benefits can be produced by incorporating honey into the composition in an amount ranging from 16 to about 26 w/w % and more preferably about 20 about 22 w/w %. As will be readily apparent to those skilled in the art, as honey and lecithin are incorporated into the composition, less soy protein will be required to ameliorate the leaching problem. All the amounts specified above are based upon the weight of the total bar. One skilled in the art will readily be able to determine these amounts based upon the teachings of the specification.

Soy protein is well known in the art and is available from many sources, such as the DuPont Chemical Company of Wilmington, Del. Co-pending U.S. patent application Ser. No. 09/107,886 filed Jun. 30, 1998 contains a detailed description regarding soy protein and the contents of this patent application is hereby incorporated by reference.

Any or all of the macro nutrients described for the liquid nutritionals may be utilized in the solid nutritionals in comparable concentrations. Aside from the required antioxidants, vitamins and minerals may also be optionally incorporated into these compositions in quantities comparable to that described for the liquid formulae. The relative caloric distribution of these solid compositions may vary widely. The protein component will typically provide from about 10% to about 50% of total calories and more preferably about 12% to about 25%. The carbohydrate component will typically provide from about 30% to about 90% of total calories and more preferably from about 50% to about 60%. The fat component will typically provide from about 5 about 50% and more typically from about 25% to about 35%.

The solid nutritional compositions may be manufactured using cold extrusion technology as is known in the art. To prepare such compositions, typically all of the powdered components will be dry blended together. Such constituents typically include the proteins, vitamin premixes, certain carbohydrates, etc. The fat soluble components are then blended together and mixed with the powdered premix above. Such fat soluble substance will include the structured lipid and any other fats incorporated into the admixture. Finally any liquid components are then mixed into the composition, forming a plastic like composition or dough.

The process above is intended to give a plastic mass which can then be shaped, without further physical or chemical changes occurring, by the procedure known as cold forming or extrusion. In this process, the plastic mass is forced at relatively low pressure through a die which confers the desired shape and the resultant exudate is then cut off at an appropriate position to give products of the desired weight.

The mass may, for example, be forced through a die of small cross-section to form a ribbon, which is carried on a belt moving at a predetermined speed under a guillotine type cutter which operates at regular intervals. The cutter, in this case, generally consists of a sharpened blade so adjusted that it cuts through the ribbon but not the underlying belt, but may also consist of a wire. In both cases, the principle is the same; the cutting process occurs at intervals that permit the moving ribbon to be cut into pieces of equivalent weight and dimensions. Generally, this is achieved by timing the cutting strokes and maintaining belt speed at an appropriate level, but there also exist computer controlled versions of this mechanism which offer greater versatility. Alternatively, the mass may be forced through a die of large cross-section and then cut at die level into slices by an oscillating knife or wire, which drop onto a moving belt and are thus transported away. The mass may also be extruded as a sheet, which is then cut with a stamp type cutter into shapes that are appropriate, such as a cookie type cutter. Finally, the mass may also be forced into chambers on a rotary die equipped with an eccentric cam that forces the thus-formed material out of the chamber at a certain point in a rotation of the cylindrical die.

After shaping, the formed product is moved by a transfer belt or other type of material conveyor to an area where it may be further processed or simply packaged. In general, a nutritional bar of the type described would be enrobed (coated) in a material that may be chocolate, a compound chocolate coating, or some other type of coating material. In all such cases, the coating material consists of a fat that is solid at room temperature, but that is liquid at temperature in excess of e.g. 88° F., together with other materials that confer the organoleptic attributes. The coating is thus applied to the bar while molten, by permitting the bar to pass through a falling curtain of liquid coating, at the same time passing over a plate or rollers which permit coating to be applied to the under surface of the bar, and excess coating is blown off by means of air jets. Finally, the enrobed bar passes through a cooling tunnel where refrigerated air currents remove heat and cause the coating to solidify.

Pharmaceutical compositions or dietary supplements may be utilized to administer the antioxidants and the structured glyceride component to the stressed individual. Suitable pharmaceutical compositions may comprise physiologically acceptable sterile aqueous or non-aqueous solutions, dispersions, suspensions or emulsions and sterile powders for reconstitution into sterile solutions or dispersions for ingestion. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the maintenance of the required particle size in the case of dispersions and by the use of surfactants. It may also be desirable to include isotonic agents, for example sugars, sodium chloride and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms such as tablets and capsules can be prepared using techniques well known in the art. For example, the antioxidants and structured glyceride component can be tableted with conventional tablet bases such as lactose, sucrose, and cornstarch in combination with binders such as acacia, cornstarch or gelatin, disintegrating agents such potato starch or alginic acid and a lubricant such as stearic acid or magnesium stearate. Capsules can be prepared by incorporating these excipients into a gelatin capsule along with the antioxidants and the structured glyceride component. The amount of the antioxidants and structured glyceride component that should be incorporated into the pharmaceutical formulation should fit within the guidelines discussed above in the summary section. As used herein, the terms pharmaceutical composition and dietary supplement should be considered interchangeable.

As described above, the invention is directed to either preventing or reducing the suppression of an immune system that is associated with stress. As used in this application stress refers to adverse stimulus that may be physical, emotional, mental, external or internal and that tends disturb the individuals homeostasis. Examples of stress include physical activity such as work or exercise, emotional such bereavement or job insecurity concerns, chronic mental or physical illnesses, health difficulties, etc. Any external or internal stimuli, or combination thereof, that causes the individual anxiety and correspondingly is capable of leading to a suppression of the immune system should be considered to be stress for the purpose of this invention.

Stress is associated with detrimental effects on the immune system. There is a clear reduction in the responsiveness of lymphocytes during periods of stress. Further, there is also an increased incidence of infection during stress. The nutritional and pharmaceutical compositions of this invention will have a beneficial effect upon the immune system of the stressed individual. These compositions will decrease the rate of infection as well as preventing or minimizing the decreases in lymphocyte responsiveness.

When the nutritional or pharmaceutical compositions according to this invention are consumed in a therapeutically effective amount, the level of stress induced suppression or dysregulation of the immune system is reduced. Those skilled in art will appreciate that effective amounts of the immunonutritional will depend on factors such as the age and weight of the individual. For the typical 70 kg human male, the therapeutically effective daily dose is at least 200 IU of Vitamin E, 50 $\mu$g of selenium, 250 mg of Vitamin C, 7.5 mg of $\beta$-Carotene and 1.0 gm of structured glyceride.

A further aspect of the invention relates to reducing the incidence of infection in an animal through the administration of the inventive composition to the animal. Infection is an invasion and multiplication by microorganisms, such as viruses and bacteria, in body tissues, that may be clinically inapparent or result in local cellular injury due to competitive metabolism, toxins, intracellular replication, or antigen-antibody response. In Example 2 below, the composition of this invention is demonstrated to be highly effective in reducing the incidence of upper respiratory disease (both viral and bacterial) in a human.

As used in this application, the term "treat" refers to either preventing, or reducing the incidence of, the undesired occurrence. For example, to treat immune suppression refers to either preventing the occurrence of this suppression or reducing the amount of such suppression. The terms "patient" and "individual" are being used interchangeably and both refer to an animal. The term "animal" as used in this application refers to any warm blooded mammal including, but not limited to, dogs, humans, monkeys, and apes. As used in the application the term "about" refers to an amount varying from the stated range or number by a reasonable amount depending upon the context of use. Any numerical number or range specified in the specification should be considered to be modified by the term about.

"Dose" and "serving" are used interchangeably and refer to the amount of the nutritional or pharmaceutical composition ingested by the patient in a single setting and designed to deliver effective amounts of the antioxidants and the structured triglyceride. As will be readily apparent to those skilled in the art, a single dose or serving of the liquid nutritional powder should supply the amount of antioxidants and structured glyceride discussed above in the Summary of the Invention Section. The amount of the dose or serving should be a volume that a typical adult can consume in one sitting. This amount can vary widely depending upon the age, weight, sex or medical condition of the patient. However as a general guideline, a single serving or dose of a liquid nutritional product should be considered as encompassing a volume from 100 to 600 ml, more preferably from 125 to 500 ml and most preferably from 125 to 300 ml. For a solid composition, the amount that can be consumed in a single setting is typically one bar, cookie, cracker etc. The weight of such a composition can vary from 27 to about 165 grams, and more preferably from about 60 to about 100 grams.

The following non-limiting Examples will further illustrate the present invention.

EXAMPLE 1

Preparation of Antioxidant System

In this experiment, two (2) liquid products were prepared to evaluate the stress-induced immune suppression in a human being. Table 1 sets out the bill of materials for a batch of the Control and Experimental formulas.

TABLE 1

BILL OF MATERIALS
Antioxidant System - Formulations

| Ingredient | Control (Kg) | Experimental (Kg) |
|---|---|---|
| Protein | 9.59 | 9.59 |
| Corn Oil | 5.653 | 5.653 |
| Soy Lecithin | 0.235 | 0.235 |
| Sucrose | 22.083 | 22.083 |
| Orange Flavor | 2.857 | 3.402 |
| Potassium Citrate | 1.493 | 0.75 |
| Water | 411.399 | 409.374 |
| *Coloring | 0.286 | — |
| Ascorbic Acid | — | 1.225 |
| Vitamin E (D-α-tocopherol) | — | 0.332 |
| 45% KOH | — | 0.857 |
| 30% β-Carotene | — | 0.095 |
| Na Selenite | — | 0.00043 |
| TOTAL | 453.6 | 453.6 |

*Color was added to the Control product to match the color of the Experimental product containing β-Carotene. This was necessary to blind the study subjects.

The raw materials for the Control and Experimental formulas were from commercial suppliers and were of food grade quality. The formulas were prepared by mixing a fat slurry and a protein slurry. The fat blend slurry was prepared by heating corn oil to a temperature in the range of 54–68° C. with agitation. An emulsifier (soy lecithin) was then added under agitation and allowed to dissolve. The products were manufactured using soy lecithin distributed by Central Soya, Incorporated, Fort Wayne, Ind., U.S.A. under the trade designation "Centrol CA". The 30% β-Carotene and vitamin E (D-α-tocopherol acetate) were then added to the slurry with agitation. The completed slurry was held under moderate agitation at a temperature in the range of 54–68° C. for a period of no longer than twelve (12) hours until it was blended with the other slurries.

A protein-in-water (PIW) slurry was prepared by heating about half of the water to a temperature in the range of 63–71° C. with agitation and the sodium caseinate was then added. The products were manufactured using sodium caseinate protein distributed by MD Foods Ingredients Incorporated, 2480 Morris Avenue, Union, N.J. U.S.A.

The completed PIW slurry was held under moderate agitation at a temperature in the range of 60–71° C. for a period of no longer than four hours until final blending.

The oil blend slurry was added to the PIW slurry and the sugar (sucrose) was added with agitation. The potassium citrate was then slowly added with agitation and the resultant blend was held for no less than five (5) minutes before a preprocess blend pH was taken. The preprocessed blended slurry was maintained at a temperature in the range of about 60–71° C.

After a period of not less than one minute nor greater than two (2) hours, the blended slurry was subjected to deaeration, Ultra-High-Temperature (UHT) heat treatment and homogenization, as described below:

A. Heat the blended slurry to a temperature in the range of 65–71° C.;

B. Deaerate the blend to 25.4–38.1 cm Hg;

C. Emulsify the blended slurry at 63–77 atmospheres; and

D. Pass the mix through a plate/coil heater and heat the mix to 120–122° C. with a hold time of approximately ten (10) seconds.

The Control and Experimental products were packaged in 8 ounce (241 ml) metal containers and terminally sterilized. Table 2 sets forth the target values per liter of the Control and Experimental products and an acceptable range for each component.

TABLE 2

Specification of Antioxidant System
(Values per liter)

| | Control | | Experimental | |
|---|---|---|---|---|
| Test | Target | Range | Target | Range |
| Energy, kcal | 402.4 | 382–423 | 409 | 388–429 |
| Total Solids, g | 87.2 | 82.8–91.6 | 90.3 | 85.8–98.5 |
| Fat, g | 13.6 | 12.9–14.3 | 14.3 | 13.6–15.0 |
| Protein, g | 20 | 19–21 | 20 | 19–21 |
| Carbohydrate, g | 50 | 47.5–52-5 | 50 | 47.5–52.5 |
| Ash, g | 3.6 | 0–7 | 6 | 0–10 |
| Chloride, g | 38.6 | 0–200 | 38.6 | 0–200 |
| Potassium, mg | 1225 | 1000–1500 | 1225 | 1000–1500 |
| Sodium, mg | 274.3 | 0–500 | 274.3 | 0–500 |
| Magnesium, mg | 5 | 0–20 | 4.9 | 0–20 |
| Calcium, mg | 42.6 | 0–100 | 22.7 | 0–100 |
| Phosphorus, mg | 173.4 | 0–400 | 173.4 | 0–400 |
| Vitamin C, mg | 0 | <6 | 2460 | 2119–2800 |
| Vitamin E (D-α-tocopherol), IU | 0 | <20 | 873.8 | 847.5–900 |
| β-Carotene, mg | 0 | <2 | 64.8 | 63.6–66.0 |
| Selenium, mcg | 0 | <30 | 446.9 | 423.7–470 |

Evaluation of Antioxidant System

Soldiers participating in the Special Forces Assessment and Selection School (SFAS) at Fort Bragg, N. C. were recruited to evaluate the ability of the Experimental product to reduce or alleviate the stress induced immune system degradation. The SFAS is a physically and mentally demanding course and is twenty-one (21) days in duration. Soldiers typically cover 150 miles (240 km) carrying a minimum of 45 lbs (10.5 kg) of field gear in a standard Army sack. Key stressors during the SFAS course include psychological stress, caloric insufficiency, periodic sleep restriction and intense periods of physical exertion. Fifty percent attrition from SFAS is normal for this training course. One hundred fifty (150) volunteers were briefed on the purpose of the study and the risks and benefits involved. A subset of thirty-six (36) volunteers were recruited as a reference group. This reference group was used to validate the various immunological assays used in this study. The reference group was not randomized into the study groups nor were they given the Experimental or Control beverages. Blood samples were drawn from all volunteers and skins test, as described below, were conducted prior to the initiation of the training. Subjects were stratified on the basis of smoking and then were randomly assigned into one of two treatment groups. One group received the Experimental beverage and one group was given the placebo containing no antioxidants (Control). The Control and Experimental beverages were consumed in liquid form and provided about 200 calories per day (0.4 Kcals per ml). The beverages were provided in 8 ounce (241 ml) cans and the subjects were requested to drink two cans per day.

Other measurements taken included height, weight, skin fold measurements and body fat assessments using near infrared measurements. These measurements and the blood draw were also taken at Day 20. On the day prior to the collection of blood samples, soldiers were required to take no food or fluid except plain water after 9:00 p.m. the evening preceding the blood draw.

Food intake was measured and recorded daily. The subjects were fed a mix of MREs (Meals-Ready-to-Eat) and A-rations (hot meals) plus 2 cans of the Control or Experimental beverages (except for the reference group). Data were collected using 24 hour diet records on which the subjects recorded their daily food and fluid intake. During the time the subjects were consuming A-rations, food intake was monitored using visual estimation techniques. Nutrient intakes were calculated from the food item intake forms and visual estimation food records. Data reduction and nutrient calculation were completed using a computerized analysis of nutrients system.

Blood samples were collected at baseline (Day 0) and on Day 20 in four (4) separate vacutainer tubes. The total amount of blood drawn for the study was about 68 ml. Tube 1 (13 ml SST, red top) was for measurement of key nutritional markers including energy substrates, vitamin C and biochemical markers of general health status. Tube 2 (7 ml Heparin, royal blue top) was used for selenium analysis and leukocyte analysis. One (1) ml was removed for whole blood selenium analysis and five (5) ml of whole blood was removed and mixed with a 2% solution of dextrin and allowed to sediment for thirty (30) minutes. The leukocyte rich supernatant was removed and washed. The remaining blood was used for preparation of whole blood cultures for lymphocytes blastogenesis. Tube 3 (7 ml EDTA, purple top) was used for a total blood cell count as determined on a Coulter JT blood analyzer. This analyzer was used to determine hemoglobin, hematocrit, mean corpuscular volume, white cell count, red cell count, platelet count, percent lymphocytes, percent monocytes and percent granulocytes. After the blood count was determined, the tube was centrifuged and the plasma was removed. Plasma was used for determination of vitamin A and E content. Tube 4 (7 ml, Heparin, royal blue top) was used to quantify lymphocyte subsets by flow cytometry and polymorphonucleated cell phagocytosis. Ability of the test subjects to generate in vivo immune response was assessed by administering a DTH test (Multitest-CMI, Connaught Laboratories, Inc., Swiftwater, Pa.). The test was given at the end of Day 20. The test kit contained a glycerin negative control and seven (7) antigens of culture filtrate from the following microorganisms: *Clostridium tetani* (tetanus toxoid), *Corynebacterium diphtheria* (*diphtheria* toxoid), Streptococcus Group C (streptococcus), *Mycobacterium tuberculosis* (*tuberculin*, old), *Candida Albicans* (candida antigen), *Trichonphyton mentogrophytes* (trichonphyton antigen) and *Proteus mirabilis* (proteus).

The tine test was applied to the ventral forearm of each subject in the morning, after the blood samples were taken. After 48 hours, the response to each antigen was determined by measuring the diameters (parallel and perpendicular to the long axis of the forearm) of the induration resulting at each of the eight tine administration sites. The site was recorded as a positive reaction when it showed an induration of 2 mm in diameter or more compared to a negative control.
Statistical Analyses The primary response variable in this study was the in vitro lymphocyte proliferative response. This was determined based on radioactivity of lymphocytes placed in culture and pulsed with radioactive thymidine. Statistical analysis of the data used a one tailed test with a confidence coefficient of 0.95.

Comparability of the groups at baseline was assessed and all continuous level data were examined to test the assumption of normality by fitting a one way ANOVA model and examining the residuals with the Shapiro-Wilk test. Results were considered statistically significant if the p value of the analysis was less than 0.05.
Results The results of the lymphocyte proliferation are set forth in FIG. 1. It is quite evident that the Control product (protein, lipid and carbohydrate without antioxidant system) was relatively ineffective in protecting the immune system, as evidenced by lymphocyte proliferation from the degradation caused by the stress of the SFAS. In contrast, the antioxidant system according to this invention lessened the degradation by 15% (−21% vs. −6%). (A value of −21% represents a greater reduction in immune function.) This difference between the Control and the Experimental immunonutritionals was significant at $p<0.05$.

The total induration (average sum in mm) was obtained for each subject. Subjects receiving the Control beverage had a mean induration of 4.4 mm with an SEM of 0.8 mm. The treatment group had a mean induration of 4.4 mm with an SEM of 0.5 mm. A reference group that were an aged matched military cohort were used to validate the immunological assays used in this study. The reference group had a total induration mean of 13.1 mm per subject with an SEM of 1.0 mm. The reference group was not randomized into the study groups nor were they given the Experimental or Control beverage.

From this information, it can be concluded that based on lymphocyte proliferation, supplementation of antioxidants attenuated stress-induced immune suppression. It is interesting to note that antioxidant supplementation had little effect on cell mediated immune function as determined by delayed type skin hypersensitivity. The following Example 2 demonstrates that antioxidant supplementation combined with ingestion of the disclosed structured glyceride component results in attenuation of stress-induced immune suppression as measured by both the lymphocyte proliferation and delayed type skin hypersensitivity.

EXAMPLE 2

Immunonutritional with Structured Glyceride Component

In this experiment, the nutritional status and immune changes of soldiers attending the SFAS at Fort Bragg, N.C., was studied. A Control and Experimental product were formulated to produce a ready-to-eat product that contained protein, fat, carbohydrates, vitamins and minerals. The Experimental product utilized: 1) a structured glyceride as part of the lipid component; 2) the antioxidant system in accordance with the invention; and 3) indigestible carbohydrate (i.e., FOS).

The liquid nutritional product of the present invention was manufactured by preparing three (3) slurries that are blended together, heat treated, standardized, packaged and sterilized. The process for manufacturing 4545 kg of the liquid nutritional product using the bill of materials from Table 5 is described in detail below.

A carbohydrate/mineral slurry was prepared by first heating approximately 1854 kg of water to a temperature range of about 66°–71° C. with agitation. The following minerals were then added in the order listed, under high agitation: trace/ultratrace mineral premix, potassium citrate, magnesium chloride, potassium chloride, sodium citrate, potassium iodide, zinc sulfate, cupric sulfate, sodium selenite and calcium phosphate tribasic. Maltodextrin was added to the slurry under high agitation and was allowed to dissolve while the temperature was maintained at about 63° C. The product was manufactured using maltodextrin distributed by Cerestar U.S.A. Incorporated (formerly American Maize), Hammond, Ind., U.S.A., under the trade designation "Lodex-15". The remaining sugar (sucrose) and indigestible oligosaccharides were then added under high agitation. The product was manufactured using oligosaccharide powder distributed by Golden Technologies Company, Golden, Colo., U.S.A. under the trade designation "Nutriflora-P fructooligosaccharide Powder (96%)" The completed carbohydrate/mineral slurry was held with high agitation at a temperature in the range of 60°–66° C. for no long than twelve (12) hours until it was blended with the other slurries.

A protein-in-fat (PIF) slurry was prepared by combining and heating the canola/MCT structured glyceride, soy oil and high oleic safflower oil to a temperature in the range of 32°–43° C. with agitation. The emulsifier (soy lecithin) was then added under agitation and allowed to dissolve. The product was manufactured using soy lecithin distributed by Central Soya Incorporated, Fort Wayne, Ind., U.S.A. under the trade designation "Centrol CA". The Vitamin DEK premix, vitamin A, vitamin E (D-a-tocopherol acetate), 30% β-Carotene, carrageenan and sodium caseinate were then added to the slurry with agitation. The completed PIF slurry was held under moderate agitation at a temperature in the range of 32°–43° C. for a period of no longer than twelve (12) hours until it was blended with the other slurries.

A protein-in-water (PIW) slurry was prepared by first adding the calcium caseinate to about 1172 kg of water and heating to a temperature in the range of 66°–71° C. with agitation. Sodium caseinate and soy protein isolate were then added to the calcium caseinate slurry under agitation. The product was manufactured using calcium and sodium caseinate proteins distributed by New Zealand Milk Products, Incorporated, 3637 Westwind Boulevard, Santa Rosa, Calif., U.S.A. under the trade designations "Alanate 380" and "Alanate 180" respectively and soy protein isolate distributed by Protein Technologies International, Checkerboard Square, 13T, St. Louis, Mo., U.S.A. under the trade designation "Supro 1610".

The completed PIW slurry was held under moderate agitation at a temperature in the range of 60°–66° C. for a period of no longer than four (4) hours until final blending.

The PIW and PIF slurries were blended together with agitation and the resultant blended slurry was maintained at a temperature in the range of about 54°–63° C. After waiting for at least one minute, the carbohydrate/mineral slurry was added to the blended slurry from the preceding step with agitation and the resultant blended slurry was maintained at a temperature in the range of about 54°–63° C. The vessel that contained the carbohydrate/mineral slurry was rinsed with about 4.54 kg of water and the rinse water was added to the blended slurry.

After waiting for a period of not less than one minute nor greater than two hours, the blend slurry was subjected to deaeration, Ultra-High-Temperature (UHT) heat treatment and homogenization using equipment and techniques known to the industry.

Subsequent to homogenization and cooling of the product, predefined analytical testing for quality control was conducted. Based on the analytical results, an appropriate amount of dilution water was added to the batch with agitation. A vitamin solution and flavor solution were prepared separately and added to the processed blended slurry.

The vitamin solution was prepared by heating about 31 kg of water to a temperature in the range of about 32°–43° C. with agitation, and thereafter adding the following ingredients, in the order listed, under agitation: ascorbic acid, 45% potassium hydroxide, taurine, water soluble vitamin premix, choline chloride and L-carnitine. The vitamin slurry was then added to the blended slurry under agitation.

The flavor solution was prepared by adding 2.772 grams of artificial butter and 1,386 grams of artificial pecan flavors to about 32 kg of water with agitation. The product was manufactured using artificial butter and pecan flavors distributed by Firmenich, Incorporated, Box 5880, Princeton, N.J., U.S.A. under the trade designations "Artificial Butter Flavor 596.333/T" and "Artificial Pecan Flavor 596.332/T". The flavor slurry was then added to the blended slurry under agitation.

The product pH was adjusted to achieve optimal product stability. The completed product was then placed in suitable containers and subjected to terminal sterilization.

The Control product was manufactured using a similar process, however, the bill of materials set forth in Table 3 was used.

TABLE 3

Bill of Materials for Control (4545 Kg Batch)

| Ingredient | Amount (Kg) |
| --- | --- |
| Soy Protein Isolate | 42.278 |
| Ca Caseinate | 27.911 |
| Na Caseinate | 183.560 |
| Corn Oil | 217.796 |
| Lecithin | 6.735 |
| Maltodextrin | 669.438 |
| Sucrose | 191.963 |
| K Citrate | 10.5 |
| Na Citrate | 4.5 |
| Water | 3,181.153 |
| Carrageenan | 0.163 |

1) Coloring was added to assist in blinding
2) Butter pecan flavor added
3) Caloric density 1.5 cal/ml Table 4 lists the nutrient breakdown for the Control product.

TABLE 4

Nutrient Breakdown - Control Product

| NUTRIENT | PER LITER | % OF CALORIES |
| --- | --- | --- |
| Protein, g<br>73 weight % Na Caseinate<br>11.1 weight % Ca Caseinate<br>15.9 weight % Soy Protein Isolate | 55.8 | 14.7 |
| Lipid, g<br>97 weight % Corn Oil<br>3 weight % Soy Lecithin | 54.8 | 32 |
| Carbohydrate, g<br>23 weight % Sucrose<br>77 weight % Maltodextrin | 205 | 53.3 |

Table 5 sets forth the bill of materials for the Experimental beverage.

TABLE 5

BILL OF MATERIALS FOR IMMUNONUTRITIONAL 4545 Kg Batch

| Ingredient | Amount (Kg) |
| --- | --- |
| Soy Protein Isolate | 42.278 |
| Ca Caseinate | 27.911 |
| Na Caseinate | 183.560 |
| Canola/MCT Structured glyceride | 155.537 |
| High Oleic Safflower Oil | 33.329 |
| Soy Oil | 33.329 |
| Lecithin | 6.872 |
| Maltodextrin | 645.789 |
| Fructooligosaccharide (FOS) | 78.856 |
| Sucrose | 174.636 |
| Ultra Trace and Trace Mineral Premix | 1.000 |
| Ascorbic Acid | 6.221 |
| L-Carnitine | 1.050 |
| Taurine | 1.050 |
| Vitamin A | .018 |
| Vitamin E (D-α-tocopherol acetate) | 2.800 |
| 30% β-Carotene | .470 |
| Water Soluble Vitamin Premix | .750 |
| Cupric Sulfate | .027 |
| Zinc Sulfate | 1.650 |
| Sodium Selenite | .001 |
| Vitamin D, E & K Premix | .820 |
| MgCl | 10.000 |
| Potassium Chloride | 5.000 |
| Potassium Citrate | 10.500 |
| 45% by wt. Potassium Hydroxide | 4.354 |
| Sodium Citrate | 4.500 |
| Choline Chloride | 2.200 |
| Calcium Phosphate Tribasic | 8.200 |
| Water | 3093.393 |
| Carrageenan | .163 |

Table 6 sets forth the nutritional composition of the immunonutritional according to the invention.

TABLE 6

Nutrient Breakdown - Immunonutritional

| NUTRIENT | PER LITER | % OF CALORIES |
| --- | --- | --- |
| Protein, g<br>73 weight % Na Caseinate<br>11.1 weight % Ca Caseinate<br>15.9 weight % Soy Protein Isolate | 55.8 | 14.7 |
| Lipid, g<br>67.9 weight % Structured glyceride<br>14.55 weight % High Oleic Safflower Oil<br>14.55 weight % Soy Oil<br>3.0 weight % Soy Lecithin | 56.9 | 32 |
| Carbohydrate, g<br>9 weight % FOS, g<br>71 weight % Maltodextrin<br>20 weight % Sucrose | 211<br>16.95 | 53.3 |

1) Butter Pecan flavor added
2) Coloring not required as β-Carotene provided color.

Structured Glyceride Component

An important aspect to the present invention is the use of a structured glyceride component in the immunonutritional. In this Example, the structured glyceride was a 50/50 weight % canola oil/MCT oil that had been corandomized with sodium methoxide and then deodorized at 180° C. with 8% steam. The 50/50 blend of canola/MCT structured glyceride was provided by the Stepan Company of Maywood, N.J. The fatty acid profile of the structured glyceride used in the Experimental product is set forth in Table 7.

TABLE 7

Key Fatty Acid Profile of Structured glyceride

| Fatty Acid Carbon Number | Analyzed Weight % | Specification Range - Wt. % |
| --- | --- | --- |
| C8 + C10 | 50 | 40–60 |
| C18:1 | 27.5 | 27–30.5 |
| C18:2 | 11.2 | 10–13.5 |
| C18:3 | 5.6 | 3–6 |

1) Free fatty acid content of less than 0.10 weight %
2) Peroxide value of less than 1.0 mEg/Kg Equivalent carbon number or ECN is the sum of the carbon atoms in the acyl chains of a triglyceride molecule. For example, tripalmitin (tripalmitic glycerol), that contains three (3) acyl moieties of 16 carbon atoms would have an ECN of 48. Many of the properties of food lipids can be accounted for directly in terms of their component fatty acids. Without being bound to any theory, it is speculated that the immunonutritionals of this invention that utilize structured lipids, are able, in part, to reduce stress induced immune suppression through the enhanced availability of the unique triglycerides and the oil soluble antioxidants such as vitamin E.

A significant difference between a structured glyceride and its constituent oils, lies in the molecular species of the triglyceride. The molecular species of a triglyceride can be designated through ECN. The interesterification or corandomization of the constituent oils creates new triglyceride species that are unique to the structured glyceride and are absent in the constituent oils. Table 8 sets forth the triglyceride profile of two batches of structured glyceride that were prepared by corandomizing a 50/50 blend of MCT oil and canola oil. Table 8 also presents the ECN profile for the physical mix of the MCT oil and canola oil.

TABLE 8

Triglyceride Profile of 50/50 Blend of MCT Oil and Canola Oil and the Corresponding Structured glyceride

| ECN[a] | Physical Mix % by weight | Structured glyceride - Batch 1 - % by weight | Structured glyceride - Batch 2 - % by weight |
| --- | --- | --- | --- |
| 24 | 14.9 | 5.5 | 5.4 |
| 26 | 20.3 | 10.4 | 10.2 |
| 28 | 13.4 | 4.9 | 4.8 |
| 29 | — | 1.2 | 1.3 |
| 30 | 3.1 | 1.2 | 1.1 |
| 31 | — | 0.7 | 0.8 |
| 32 | 0.2 | 0.9 | 0.9 |
| 33 + 34[b] | — | 14.0 | 13.7 |
| 35 + 36[b] | — | 16.9 | 16.6 |
| 37 + 38[b] | — | 5.6 | 5.7 |
| 40 | 0.3 | 0.5 | 0.6 |
| 41 | — | 0.9 | 0.8 |
| 42 | — | 1.6 | 1.6 |
| 43 | — | 13.7 | 13.5 |
| 45 | — | 8.7 | 8.5 |
| 47 + 48[b] | — | 0.9 | 0.9 |
| 49 + 50[b] | — | — | — |
| 51 | 0.8 | 0.6 | 0.6 |
| 52 | — | — | 0.7 |
| 53 | 5.6 | 4.0 | 3.9 |
| 54 | 34.0 | — | — |

TABLE 8-continued

Triglyceride Profile of 50/50 Blend of MCT Oil and Canola Oil and the Corresponding Structured glyceride

| ECN[a] | Physical Mix % by weight | Structured glyceride - Batch 1 - % by weight | Structured glyceride - Batch 2 - % by weight |
|---|---|---|---|
| 56 | 2.8 | 0.3 | 0.3 |
| 58 | 1.3 | 0.2 | 0.2 |
| 60 | 0.8 | — | — |

[a]ECN is Equivalent Carbon Number, sum of carbon atoms in the acyl chains on the glycerol backbone of a triglyceride.
[b]The triglyceride species pairs with same number of carbon and different degree of unsaturation were coeluted and integrated as one peak.

The values reported in Table 8 are from an actual analysis of the physical blend and the structured lipids. It is interesting to note that the two (2) batches of structured glyceride are almost identical in ECN profile. The triglycerides with ECN numbers of from 32–45 represent species that are unique to the structured triglyceride and are absent from the physical mix.

The various ingredients for the immunonutritional of the invention and the Control were combined using conventional techniques and equipment as described previously. Those skilled in the art of preparing liquid nutritional products will readily appreciate the numerous variables and processes that can be used to prepare the products. Thus, the Control and immunonutritional were prepared and packaged in 8 ounce (241 ml) metal cans and terminally sterilized.

The immunonutritional according to the invention provided 1060 mg of vitamin C per liter of product, 847 IU of vitamin E per liter of product, 32.4 mg of β-Carotene per liter of product and selenium at 211 μg per liter of product. The major minerals and all other trace and ultra trace minerals were at levels that are typically found in medical nutritional products such as Ensure Plus, produced and marketed by the Ross Products Division of Abbott Laboratories, Columbus, Ohio.

Testing 200 volunteers attending the U.S. Army SFAS course were randomly assigned to consume two (2) cans or about 16 ounces (453 g) of the Experimental immunonutritional according to this invention (n=100) or two (2) cans of the placebo (Control) beverage (n=100) with their regularly available rations (MREs and A-rations). Each beverage supplied approximately 360 Kcals/can.

The Control and Experimental product contained a similar amount of energy and macronutrients, but differed in lipid composition and micronutrient (antioxidant system) concentrations. In a manner similar to that described in Example 1, immune function in this experiment was determined by flow cytometry that measured cellular population changes and activation of lymphocytes as well as granulocyte phagocytosis. Antibodies that are highly sensitive and specific that detect cell-surface antigens were labeled with fluorescent compounds and then mixed with the isolated cells. The antibodies attach to specific antigens on the cell surfaces and thus identify a specific cell (i.e., T-cells or B-cells) or to a limited extent, function (i.e., activation and phagocytosis). A determination of upper respiratory tract infection was diagnosed by a military physician based upon an observation of involvement of any and all airways, including the nose, paranasal passages, throat, larynx, trachea or bronchi. An additional clinical measurement included delayed type hypersensitivity (administered to a subset of soldiers). Clinical observations also included febrile or non-febrile determinations. FIG. 2 sets forth the results regarding the rate of upper respiratory infection per group (i.e., control vs. treatment).

FIG. 2 evidences that the subjects consuming the immunonutritional according to the invention had a greatly reduced incidence of upper respiratory tract infection compared to the Control and non-study groups. This finding is of statistical significance and is a surprising result.

The attrition rate of subjects in this study during the SFAS was typical. Of the 100 subjects in each group, 57 controls finished and 49 of the Experimental group completed the program for a total of 106 subjects. Both groups experienced a modest weight loss of about 6 lbs per soldier. Modest differences were also seen at the end of training between the two groups in the level of T cells, B cells and NK cells. From the daily food intake records, it was determined that the Experimental group consumed 100% of all RDA established nutrients, while the Control group consumed less than 100% of the RDA for vitamins A, E and folic acid.

The group fed the Experimental immunonutritional had fewer subjects anergic to delayed type hypersensitivity (DTH) as compared to the Control group. The DTH test (Multi-Test-CMI, Connaught Laboratories, Inc., Swiftwater, Pa.) contained a glycerin negative control and seven (7) antigens as set forth in Example 1. The antigens were administered with a device similar to a tine skin test, by firm pressure against the skin. The resulting induration was measured in mm and non-responsiveness (anergy) was defined as a total response of less than or equal to 2.0 mm for all of the seven (7) test antigens. Table 9 sets forth the data collected.

TABLE 9

Total Induration (Average Sum in mm) Per Subject

| | Mean | SEM |
|---|---|---|
| Control | 7.5 | 0.9 |
| Treatment | 9.8 | 0.8 |
| *Reference | 13.1 | 1.0 |

*Reference Group was an aged match military cohort used to validate the immunological assays used in this study. The reference group was not randomized into the study groups nor were they given the Experimental or Control beverage.

From FIG. 3 and Table 9, it is quite clear that, based on lymphocyte proliferation, supplementation of antioxidants plus the structured glyceride minimized the stressed induced suppression of the immune system. There were also few subjects receiving the Experimental product that were anergic as determined by delayed type skin hypersensitivity and the response (total sum of induration) in the treatment group was greater.

It appears that the minimizing influence of the Experimental formula was the result of effect on the lymphocyte and immune cell function as no major differences were noted in circulating T-lymphocytes, B-lymphocytes, and natural killer cell numbers.

From this experiment, it was observed that the sum of the DTH responses were greater in the Experimental group and this is a most interesting finding because anergy and decreased DTH responses correlate with increased risk of infection. The results of this experiment also indicated that fewer soldiers consuming the immunonutritional of the invention experienced upper respiratory tract infection as compared to the Control group. In general, the soldiers consuming the immunonutritional according to the invention experienced fewer infections and signs of immunosuppression than those consuming the Control (containing similar amounts of macronutrients and energy).

EXAMPLE 3

A solid nutritional composition according to the present invention has been manufactured by preparing three pre-blends which are combined, formed/extruded, coated, cooled and packaged. The four step process for manufacturing approximately 234 kilograms of the bar nutritional product, using the Bill of Materials (Attachment 10), is described in detail below.

Step One

A dry blend is prepared by adding the soy protein isolates (Type One: Trade name Supro 661, supplied by Protein Technologies International, St. Louis, Mo. 63188 and Type Two: Trade name Supro 1610, from the same supplier), calcium caseinate, vitamin/mineral premix, fructooligosaccharide, oat bran, maltodextrin, corn syrup solids, crisp rice and soy polysaccharide to a double arm mixer at room temperature (24°±10° C.) and agitated for approximately 200 strokes.

Step Two

An oil pre-blend is prepared by combining canola/MCT structured lipid and soy lecithin in a separate mixer and blending for two minutes at room temperature (24°±10° C.). The oil blend is added to the dry blend (described in Step One) and agitated for approximately 200 strokes.

Step Three

A liquid pre-blend is prepared by adding high fructose corn syrup, crystalline fructose, glycerine, honey and artificial graham Flavor to a separate mixer and agitating for five minutes. The liquid pre-blend is added to the dry blend (described in Step One) and agitated for approximately 100 (or until a uniform dough is obtained).

Step Four

The dough is transferred to a former where the "core" bars are formed and cut to a weight of 57 grams ±2 grams. The core is coated with a melted (46–48° C.) chocolate confectionery coating so that the core + coating will attain a minimal weight of 65.0 grams and not exceed a maximum weight of 77.0 grams (targeting 68.0 grams). The bars are then cooled to a temperature between 0° and 15° C. At no time are the bars subjected to elevated temperatures for baking. The bars are then packaged in a low density polyethylene/foil wrap. More detailed information regarding the composition is shown in Table 12.

TABLE 10

| Ingredient | Quantity | |
|---|---|---|
| Nomenclature | Kilograms | Grams |
| Soy Protein Isolate (Type One) | 9.20 | 9200.0 |
| Soy Protein Isolate (Type Two) | 9.20 | 9200.0 |
| Calcium Caseinate | 16.60 | 16600.0 |
| Vitamin/Mineral Premix (see Table 11) | 10.62 | 10620.0 |
| Oat Bran | 10.00 | 10000.0 |
| Maltodextrin (10 DE) | 4.10 | 4100.0 |
| Corn Syrup Solids (20 DE) | 5.50 | 5500.0 |
| Crisp Rice | 15.34 | 15340.0 |
| Soy Polysaccharide | 12.00 | 12000.0 |
| Canola/MCT Structured Lipid | 20.00 | 20000.0 |
| Soy Lecithin | 2.00 | 2000.0 |
| High Fructose Corn Syrup | 25.00 | 25000.0 |
| Crystalline Fructose | 5.94 | 5940.0 |
| Glycerine | 5.00 | 5000.0 |

TABLE 10-continued

| Ingredient | Quantity | |
|---|---|---|
| Nomenclature | Kilograms | Grams |
| Pasteurized Honey | 32.60 | 32600.0 |
| Fructooligosaccharide Powder | 14.60 | 14600.0 |
| Artificial Gram Flavor | 0.30 | 300.0 |
| Chocolate Confectionery Coating | 35.85 | 35849.1 |
| Total Batch Weight | 233.85 | 233,849.1 |

TABLE 11

| Component | Target Per 100 grams |
|---|---|
| Beta-Carotene, mg | 275.80 |
| Vitamin D, IU | 2,847.00 |
| Vitamin E (RRR), IU | 7,096.00 |
| Vitamin K1, mcg | 422.60 |
| Vitamin C, mg | 11,968.00 |
| Folic Acid, mcg | 11,345.00 |
| Thiamine, mg | 72.97 |
| Riboflavin, mg | 68.96 |
| Vitamin B6, mg | 72.97 |
| Vitamin B12, mcg | 242.40 |
| Niacin, mg | 553.90 |
| Choline, mg | 3,670.00 |
| Biotin, mcg | 9,743.00 |
| Pantothenic Acid, mg | 324.70 |
| Sodium, mg | 5,215.00 |
| Potassium, mg | 11,879.00 |
| Chloride, mg | 11,323.00 |
| Calcium, mg | 2,514.00 |
| Phosphorus, mg | 1,887.00 |
| Magnesium, mg | 1,633.00 |
| Iodine, mcg | 1,014.00 |
| Manganese, mg | 36.04 |
| Copper, mg | 28.70 |
| Zinc, mg | 891.90 |
| Iron, mg | 113.00 |
| Selenium, mcg | 1,849.00 |
| Chromium, mcg | 714.10 |
| Molybdenum, mcg | 1,143.00 |
| L-Carnitine, mg | 1,866.00 |
| Taurine, mg | 1,866.00 |

TABLE 12

Developmental Specifications (per 100 grams)

| Nutrient | Target 65 g Bar | Target per 100 g | Developmental Specification per 100 g |
|---|---|---|---|
| Protein, g | 10.1 | 15.5 | 14.0–17.0 |
| Fat, g | 9.5 | 14.6 | 13.1–16.1 |
| Carbohydrate, g | 39.8 | 61.3 | 55.2–67.4 |
| Energy, Calories | 285 | 439 | 395–483 |
| Ash, g | 1.7 | 2.7 | 2.0–5.0 |
| Moisture, g | 3.9 | 5.9 | 2.0–10.0 |
| FOS, g | 4 | 6.2 | 5.0–7.4 |
| Beta-Carotene, mg | 8.1 | 12.4 | 11.2–13.6 |
| Vitamin D, IU | 83 | 128 | 102–154 |
| Vitamin E (RRR), IU | 207 | 319 | 287–351 |
| Vitamin K, mcg | 20.1 | 31 | 20.8–54.7 |
| Vitamin C, mg | 350 | 538 | 386–646 |
| Folic Acid, mcg | 332 | 510 | 408–612 |
| Thiamine (Vit B1), mg | 2.13 | 3.28 | 1.55–3.94 |
| Riboflavin (Vit B2), mg | 2.01 | 3.1 | 1.75–3.72 |
| Vitamin B6, mg | 2.13 | 3.28 | 2.05–3.94 |
| Vitamin B12, mcg | 7.11 | 10.9 | 6.17–13.1 |
| Niacin, mg | 16.2 | 24.9 | 19.9–29.9 |
| Choline, mg | 107 | 165 | 132–250 |

TABLE 12-continued

Developmental Specifications (per 100 grams)

| Nutrient | Target 65 g Bar | Target per 100 g | Developmental Specification per 100 g |
|---|---|---|---|
| Biotin, mcg | 284 | 438 | 308–526 |
| Pantothenic Acid, mg | 9.5 | 14.6 | 10.3–17.5 |
| Sodium, mg | 260 | 400 | 320–480 |
| Potassium, mg | 455 | 700 | 560–840 |
| Chloride, mg | 441 | 678 | 542–814 |
| Calcium, mg | 176 | 271 | 217–325 |
| Phosphorus, mg | 171 | 262 | 210–314 |
| Magnesium, mg | 75.5 | 116 | 92.8–139 |
| Iodine, mcg | 29.6 | 45.6 | 36.5–80.0 |
| Manganese, mg | 1.05 | 1.62 | 1.30–1.94 |
| Copper, mg | 0.84 | 1.29 | 1.03–1.55 |
| Zinc, mg | 26.1 | 40.1 | 32.1–48.1 |
| Iron, mg | 3.3 | 5.08 | 4.06–6.50 |
| Selenium, mcg | 54 | 83.1 | 66.5–99.7 |
| Chromium, mcg | 20.9 | 32.1 | 25.7–55.0 |
| Molybdenum, mcg | 33.4 | 51.4 | 41.1–90.0 |
| Carnitine, mg | 54.5 | 83.9 | 67.1–100.7 |
| Taurine, mg | 54.5 | 83.9 | 67.1–100.7 |

EXAMPLE 4

Immunonutritonal with Structured Glyceride Component in a Bar Food Form

As noted in Examples 1 and 2, vigorous Army training involves physical and psychological stress that causes immune dysregulation and increased risk of infection. In this Example, the nutritional status and immune changes of soldiers attending Ranger Training (RT), Fort Benning, Ga. were studied. RT (as previously described by Bernton et al.) is a longer training course (62 days) as compared to SFAS (21 days, as studied in examples 1 and 2). A Control and Experimental product were formulated as a food bar that contained protein, fat, carbohydrates, vitamins and minerals. The Experimental bar was similar in nutrient profile to the experimental product of example 2 and utilized: 1) a structure glyceride as part of the lipid component; 2) the antioxidant system in accordance with the invention; and 3) indigestible carbohydrate (ie., FOS), and 4) other vitamins and minerals. Three experimental bars were identical in composition and manufactured according to the process outlined in Example 3. The control bars were identical to the experimentals except that no vitamin and mineral premix was added and the fat was corn oil.

Testing

One hundred twenty-three soldiers participating in U.S. Army Ranger Training volunteered and were randomly assigned to consume two (2) bars or about 150 g/day of Experimental immunonutrition bar according to this invention (n=63) or two (2) bars of the placebo (control) bar (n=60). Nutritional status (body weight) and Immune function (flow cytometry, response to hepatitis A vaccination, DTH) was evaluated throughout Ranger Training. The effect of the stress as well as nutritional product was assessed as a change from baseline to each time point (visit 2-baseline; visit 3-baseline; visit 4-baseline) of important immune cells and lymphocytes. We screened subjects for previous exposure or vaccination to hepatitis A and then vaccinated the remaining subjects. Furthermore we administered a DTH to a group of soldiers before and after the stressful training.

It was a most unexpected find that the subjects of this study actually gained weight (FIG. 4) during this intense physical training. This weight gain was partially attributed to the extra energy of the experimental and control bars. In previous studies, we found that soldiers typically lost 20 to 30 pounds. Benton et. al found similar weight loss of 20–30 pounds during RT. There was a trend toward greater weight gain in the treatment group (P=0.067). Therefore, it appears that some of the nutrients contained in the Experimental bar helped soldiers maintain weight as compared to the Control group.

Significant changes in T-cells, B-cells and NK cell numbers and cellular activity occurred within each group as a result of the vigorous stress. There was evidence that the subjects consuming the Experimental bar experienced less of a decline in a number of important immune cells. For example, there was less of a decline in the number of monocytes in the soldiers under the most stressful time of the Ranger Training course (P<0.013). Furthermore, there was evidence that the experimental bar attenuated the stress induced loss of important lymphocytes (T-lymphocytes, *P=0.023) from Experimental vs. the Control Group (FIG. 5). The decrease was the result of the loss of CD4+ (helper) lymphocytes which play a pivotal role in the response of the immune system (FIG. 6, *p=0.008). There was also less of a decline of Th1 lymphocytes (lymphocytes that produce interferon-gamma upon stimulation) in the subjects that consumed the Experimental product (FIG. 7, *P=0.029). A short survey was also administered to understand the subject's preference to the bar and its acceptance during RT. Seventy-five percent of the subjects indicated that the Experiment bar helped them to complete RT, while only 67% of Control subjects indicated that it was helpful. There was no statistical difference in DTH or response to vaccine between the groups, although both vaccine and DTH response was suppressed. Thus these findings support that the invention plays a role in minimizing the stress induced immune changes which place soldiers at increased risk of infection.

Industrial Applicability

The medical community continues to seek methods and compositions useful in overcoming the problems associated with emotional and physical stress. Stress is well known to compromise the immune system in an animal and thereby make the animal more susceptible to disease. For example, in a study of 586 hospital patients, it was found that DTH anergy is associated with a sepsis rate of 45% and a mortality rate of 38% compared with 7% sepsis and 3% death rates in reactive patients. Thus, methods and products that protect the immune system and/or lessen its degradation will fulfill a long felt need. The need to provide adequate protection to stressed individuals such as soldiers, athletes who exercise excessively and the chronically ill has been well documented. The novel immunonutritionals of this invention have been shown to be highly effective in reducing the amount of immunosuppression that occurs in the stressed individual. The method of the present invention can be conveniently accomplished through the administration of pills, capsules, dietary supplements, enteral nutritionals and the like.

The foregoing examples are merely illustrative and not intended to limit the scope of the invention as described by the following claims. Modifications and alternative embodiments of the invention will be apparent to those skilled in the art in view of the foregoing description. Accordingly, this description is to be construed as illustrative only and is for the purpose of teaching those of skill in the art the manner of carrying it out.

We claim:

1. A single serving solid nutritional composition comprising:
   a) the following antioxidants, present in at least about the following amounts, on a per serving basis:
      i) 250 mg of vitamin C;
      ii) 200 iu of vitamin E;
      iii) 50 mcq of selenium;
      iv) 7.5 mg of β-Carotene, and;
   b) at least one gram of a structured glyceride component, characterized in that it contains about 50% by weight or more of triglyceride species and at least 40% by weight of the triglyceride species have:
      (i) about 33 to 70 wt. % of acyl moieties having 4 to 12 carbon atoms;
      (ii) about 30 to 67 wt. % of acyl moieties having more than 12 carbon atoms, and;
      (iii) an equivalent carbon number of greater than 30 to less than 48 and;
   c) a protein component providing from about 10 to about 50% of the total calories of the composition.

2. The composition according to claim 1 which additionally contains zinc at a concentration of at least about 12.5 mg of zinc per serving.

3. The composition according to claim 1 which additionally contains at least about 0.8 mg of copper per serving.

4. The composition according to claim 1 which additionally contains at least about 100 ug of folic acid per serving.

5. The composition according to claim 1 wherein said structured glyceride component predominantly comprises triglycerides.

6. The composition according to claim 5 wherein said triglycerides comprise 45 to 70 wt. % of acyl moieties having 4 to 12 carbon atoms.

7. The composition according to claim 5 wherein said triglycerides comprise 30 to 55 wt. % of acyl moieties having more than 12 carbon atoms.

8. The composition according to claim 5 wherein said triglycerides comprise 50 to 65 wt. % of acyl moieties having 4 to 12 carbon atoms and 35 to 50 wt. % of acyl moieties having more than 12 carbon atoms.

9. The composition according to claim 1 wherein said triglycerides have an equivalent carbon number of about 32 to about 42.

10. The composition according to claim 1 wherein said composition additionally contains at least one further ingredient selected from the group consisting of carbohydrates, lipids, minerals, FOS, dietary fibers, and vitamins.

11. The composition according to claim 1 wherein said antioxidants and said structured glyceride component are present in the following amounts:
   a) 200–1000 IU of vitamin E per serving;
   b) 50–400 µg of selenium per serving;
   c) 500 mg–5 g of vitamin C per serving;
   d) 7.5–50 mg of β-Carotene per serving, and;
   h) 1–100 gm of said structured glyceride component per serving.

12. A method of reducing immune suppression in an animal caused by stress, said method comprising administering to said animal a composition according to claim 1.

13. A method of reducing the incidence of infection in an animal, said method comprising administering to said animal a composition according to claim 1.

14. A method of normalizing the immunological status of an animal, said method comprising administering to said animal a composition according to claim 1.

15. A method of reducing stress induced immunological dysregulation in an animal, said method comprising the administration to said animal a composition according to claim 1.

16. A method for providing nutritional support to a stressed individual comprising the administration of a composition according to claim 1.

17. The composition according to claim 1 in which said composition is a bar.

18. The composition according to claim 1 in which said composition is a cookie.

19. The composition according to claim 1 in which said composition is a cracker.

20. The composition according to claim 1 in which said protein component includes one or more soy proteins.

21. The composition according to claim 20, in which said soy protein is present in an amount ranging from about 4 to about 20 by weight of the composition, based upon the total weight of the composition.

22. The composition according to claim 21 further comprising honey, which is present in the amount of from about 16 to about 26 percent by weight, based upon the total weight of the composition.

23. The composition according to claim 1 further comprising a carbohydrate component, which is present in an amount sufficient to provide from about 30 to about 90% of total calories.

24. The composition according to claim 1 having a total mass ranging from about 27 to about 165 grams.

25. The composition according to claim 1 having a total mass ranging from about 60 to about 100 grams.

26. The composition according to claim 1 wherein said antioxidants and said structured glyceride component are present in the following amounts:
   a) 200–600 IU of vitamin E per serving;
   b) 100–200 µg of selenium per serving;
   c) 1–3 g of vitamin C per serving;
   d) 15–35 mg of β-Carotene per serving, and;
   e) 10–50 gm of said structured glyceride component per serving.

* * * * *